US006558913B1

(12) United States Patent
Bertina et al.

(10) Patent No.: US 6,558,913 B1
(45) Date of Patent: *May 6, 2003

(54) METHOD FOR SCREENING FOR THE PRESENCE OF GENETIC DEFECT ASSOCIATED WITH THROMBOSIS AND/OR POOR ANTICOAGULANT RESPONSE TO ACTIVATED PROTEIN C

(75) Inventors: Rogier Maria Bertina, Leiden (NL); Pieter Hendrik Reitsma, Leiden (NL)

(73) Assignee: Akzo Nobel, N.V. (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,019

(22) Filed: Sep. 30, 1998

Related U.S. Application Data

(60) Continuation of application No. 09/165,019, filed on Sep. 30, 1998, which is a division of application No. 08/545,353, filed on Jun. 6, 1995.

(30) Foreign Application Priority Data

Feb. 14, 1994 (EP) ............................................. 94200377

(51) Int. Cl.⁷ ............................. C12Q 1/56; C12Q 1/68; C07H 21/02; C07H 21/04
(52) U.S. Cl. ........................... 435/13; 435/6; 536/23.1; 536/24.3
(58) Field of Search ................. 435/6, 13, 76, 435/77, 78; 536/23.1, 24.3

(56) References Cited

U.S. PATENT DOCUMENTS

| | | | | |
|---|---|---|---|---|
| 5,443,960 A | * | 8/1995 | Dahlback ...................... | 435/13 |
| 5,639,726 A | * | 6/1997 | Lawrence et al. .............. | 514/12 |
| 5,705,395 A | * | 1/1998 | Griffin et al. .................. | 436/69 |
| 5,766,869 A | * | 6/1998 | Arkel et al. .................... | 435/13 |
| 5,863,896 A | * | 1/1999 | Rosing et al. ................. | 514/12 |
| 5,874,256 A | * | 2/1999 | Bertina et al. .............. | 435/69.6 |
| 5,922,855 A | * | 7/1999 | Liskay et al. | |
| 6,083,905 A | * | 7/2000 | Voorberg et al. .............. | 514/2 |
| 6,090,570 A | * | 7/2000 | Kraus .......................... | 435/13 |

FOREIGN PATENT DOCUMENTS

| | | |
|---|---|---|
| EP | 0711838 | 5/1996 |
| WO | WO 91/02812 | 3/1991 |
| WO | WO 93/10261 | 5/1993 |
| WO | WO9417415 | 5/1994 |
| WO | WO9529259 | 11/1995 |
| WO | WO9615457 | 5/1996 |
| WO | WO9630546 | 10/1996 |

OTHER PUBLICATIONS

B. Dahlback et al., *Thrombosis and Haemostasis*, 65:6:658, Jun. 1991.
T. Koster et al., *Lancet*, 432:8886:1503–1506, Dec. 18, 1993.
N.L.L. Shen et al., *The Journal of Immunology*, 150:7:2992–3001, Apr. 1, 1993.
M. Kalafatis et al., *Blood*, 82:10S1:58A, Abstract 222, 1993.
R.J. Jenny et al., *P.N.A.S.*, USA, 84:4846–4850, 1987.
J.S. Greengard et al., *Lancet*, 343:8909:1361–1362, May 28, 1994.
R.M. Bertina et al., *Nature*, 369:6475:64–67, May 5, 1994.
Mok et al., *BioTechniques*, 14(5):790–793, 1993.
Kogan et al., *PCR Protocols*, pp. 288–299, Ed Innis et al., 1990.
Voorberg et al, *Lancet*, 343:1535–1536 (Jun., 1994).
Zoller et al, *Lancet*, 343:1536–1538 (Jun., 1994).
Tuddenham, *Lancet*, 343:1515–1516 (Jun., 1994).
Beauchamp et al, *Lancet*, 344:694–695 (Sep., 1994).

* cited by examiner

*Primary Examiner*—Ethan Whisenant
(74) *Attorney, Agent, or Firm*—Myers Bigel Sibley & Sajovec

(57) ABSTRACT

Method for screening for the presence of a genetic defect associated with thrombosis and/or poor anticoagulant response to activated protein C (APC). The method is directed at detecting one or more mutations at one or more of the cleavage and/or binding sites for APC of Factor V and/or Factor Va or at Factor VIII and/or Factor VIIIa at either nucleic acid or protein level or both.

15 Claims, No Drawings

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 6909 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 1:

```
GAATTCCGCA GCCCGGAGTG TGGTTAGCAG CTCGGCAAGC GCTGCCCAGG TCCTGGGGTG      60

GTGGCAGCCA GCGGGAGCAG GAAAGGAAGC ATGTTCCCAG GCTGCCCACG CCTCTGGGTC     120

CTGGTGGTCT TGGGCACCAG CTGGGTAGGC TGGGGGAGCC AAGGGACAGA AGCGGCACAG     180

CTAAGGCAGT TCTACGTGGC TGCTCAGGGC ATCAGTTGGA GCTACCGACC TGAGCCCACA     240

AACTCAAGTT TGAATCTTTC TGTAACTTCC TTTAAGAAAA TTGTCTACAG AGAGTATGAA     300

CCATATTTTA AGAAAGAAAA ACCACAATCT ACCATTTCAG GACTTCTTGG GCCTACTTTA     360

TATGCTGAAG TCGGAGACAT CATAAAAGTT CACTTTAAAA ATAAGGCAGA TAAGCCCTTG     420

AGCATCCATC CTCAAGGAAT TAGGTACAGT AAATTATCAG AAGGTGCTTC TTACCTTGAC     480

CACACATTCC CTGCGGAGAA GATGGACGAC GCTGTGGCTC CAGGCCGAGA ATACACCTAT     540

GAATGGAGTA TCAGTGAGGA CAGTGGACCC ACCCATGATG ACCCTCCATG CCTCACACAC     600

ATCTATTACT CCCATGAAAA TCTGATCGAG GATTTCAACT CGGGGCTGAT TGGGCCCCTG     660

CTTATCTGTA AAAAGGGGAC CCTAACTGAG GGTGGGACAC AGAAGACGTT TGACAAGCAA     720

ATCGTGCTAC TATTTGCTGT GTTTGATGAA AGCAAGAGCT GGAGCCAGTC ATCATCCCTA     780

ATGTACACAG TCAATGGATA TGTGAATGGG ACAATGCCAG ATATAACAGT TTGTGCCCAT     840
```

```
GACCACATCA GCTGGCATCT GCTGGGAATG AGCTCGGGGC CAGAATTATT CTCCATTCAT    900

TTCAACGGCC AGGTCCTGGA GCAGAACCAT CATAAGGTCT CAGCCATCAC CCTTGTCAGT    960

GCTACATCCA CTACCGCAAA TATGACTGTG GGCCCAGAGG GAAAGTGGAT CATATCTTCT   1020

CTCACCCCAA AACATTTGCA AGCTGGGATG CAGGCTTACA TTGACATTAA AAACTGCCCA   1080

AAGAAAACCA GGAATCTTAA GAAAATAACT CGTGAGCAGA GGCGGCACAT GAAGAGGTGG   1140

GAATACTTCA TTGCTGCAGA GGAAGTCATT TGGGACTATG CACCTGTAAT ACCAGCGAAT   1200

ATGGACAAAA AATACAGGTC TCAGCATTTG GATAATTTCT CAAACCAAAT TGGAAAACAT   1260

TATAAGAAAG TTATGTACAC ACAGTACGAA GATGAGTCCT TCACCAAACA TACAGTGAAT   1320

CCCAATATGA AGAAGATGG GATTTTGGGT CCTATTATCA GAGCCCAGGT CAGAGACACA   1380

CTCAAAATCG TGTTCAAAAA TATGGCCAGC CGCCCCTATA GCATTTACCC TCATGGAGTG   1440

ACCTTCTCGC CTTATGAAGA TGAAGTCAAC TCTTCTTTCA CCTCAGGCAG GAACAACACC   1500

ATGATCAGAG CAGTTCAACC AGGGGAAACC TATACTTATA AGTGGAACAT CTTAGAGTTT   1560

GATGAACCCA CAGAAAATGA TGCCCAGTGC TTAACAAGAC CATACTACAG TGACGTGGAC   1620

ATCATGAGAG ACATCGCCTC TGGGCTAATA GGACTACTTC TAATCTGTAA GAGCAGATCC   1680

CTGGACAGGC GAGGAATACA GAGGGCAGCA GACATCGAAC AGCAGGCTGT GTTTGCTGTG   1740

TTTGATGAGA ACAAAAGCTG GTACCTTGAG GACAACATCA ACAAGTTTTG TGAAAATCCT   1800

GATGAGGTGA ACGTGATGA CCCCAAGTTT TATGAATCAA ACATCATGAG CACTATCAAT   1860

GGCTATGTGC CTGAGAGCAT AACTACTCTT GGATTCTGCT TTGATGACAC TGTCCAGTGG   1920

CACTTCTGTA GTGTGGGGAC CCAGAATGAA ATTTTGACCA TCCACTTCAC TGGGCACTCA   1980

TTCATCTATG GAAAGAGGCA TGAGGACACC TTGACCCTCT TCCCCATGCG TGGAGAATCT   2040

GTGACGGTCA CAATGGATAA TGTTGGAACT TGGATGTTAA CTTCCATGAA TTCTAGTCCA   2100

AGAAGCAAAA AGCTGAGGCT GAAATTCAGG GATGTTAAAT GTATCCCAGA TGATGATGAA   2160

GACTCATATG AGATTTTTGA ACCTCCAGAA TCTACAGTCA TGGCTACACG GAAAATGCAT   2220

GATCGTTTAG AACCTGAAGA TGAAGAGAGT GATGCTGACT ATGATTACCA GAACAGACTG   2280

GCTGCAGCAT TAGGAATTAG GTCATTCCGA AACTCATCAT TGAACCAGGA AGAAGAAGAG   2340

TTCAATCTTA CTGCCCTAGC TCTGGAGAAT GGCACTGAAT TCGTTTCTTC GAACACAGAT   2400

ATAATTGTTG GTTCAAATTA TTCTTCCCCA AGTAATATTA GTAAGTTCAC TGTCAATAAC   2460

CTTGCAGAAC CTCAGAAAGC CCCTTCTCAC CAACAAGCCA CCACAGCTGG TTCCCCACTG   2520

AGACACCTCA TTGGCAAGAA CTCAGTTCTC AATTCTTCCA CAGCAGAGCA TTCCAGCCCA   2580

TATTCTGAAG ACCCTATAGA GGATCCTCTA CAGCCAGATG TCACAGGGAT ACGTCTACTT   2640

TCACTTGGTG CTGGAGAATT CAGAAGTCAA GAACATGCTA AGCGTAAGGG ACCCAAGGTA   2700

GAAAGAGATC AAGCAGCAAA GCACAGGTTC TCCTGGATGA AATTACTAGC ACATAAAGTT   2760

GGGAGACACC TAAGCCAAGA CACTGGTTCT CCTTCCGGAA TGAGGCCCTG GGAGGACCTT   2820

CCTAGCCAAG ACACTGGTTC TCCTTCCAGA ATGAGGCCCT GGGAGGACCC TCCTAGTGAT   2880

CTGTTACTCT TAAAACAAAG TAACTCATCT AAGATTTTGG TTGGGAGATG GCATTTGGCT   2940

TCTGAGAAAG GTAGCTATGA AATAATCCAA GATACTGATG AAGACACAGC TGTTAACAAT   3000

TGGCTGATCA GCCCCCAGAA TGCCTCACGT GCTTGGGGAG AAAGCACCCC TCTTGCCAAC   3060

AAGCCTGGAA AGCAGAGTGG CCACCCAAAG TTTCCTAGAG TTAGACATAA ATCTCTACAA   3120

GTAAGACAGG ATGGAGGAAA GAGTAGACTG AAGAAAAGCC AGTTTCTCAT TAAGACACGA   3180

AAAAAGAAAA AAGAGAAGCA CACACACCAT GCTCCTTTAT CTCCGAGGAC CTTTCACCCT   3240
```

-continued

```
CTAAGAAGTG AAGCCTACAA CACATTTTCA GAAAGAAGAC TTAAGCATTC GTTGGTGCTT    3300
CATAAATCCA ATGAAACATC TCTTCCCACA GACCTCAATC AGACATTGCC CTCTATGGAT    3360
TTTGGCTGGA TAGCCTCACT TCCTGACCAT AATCAGAATT CCTCAAATGA CACTGGTCAG    3420
GCAAGCTGTC CTCCAGGTCT TTATCAGACA GTGCCCCCAG AGGAACACTA TCAAACATTC    3480
CCCATTCAAG ACCCTGATCA AATGCACTCT ACTTCAGACC CCAGTCACAG ATCCTCTTCT    3540
CCAGAGCTCA GTGAAATGCT TGAGTATGAC CGAAGTCACA AGTCCTTCCC CACAGATATA    3600
AGTCAAATGT CCCCTTCCTC AGAACATGAA GTCTGGCAGA CAGTCATCTC TCCAGACCTC    3660
AGCCAGGTGA CCCTCTCTCC AGAACTCAGC CAGACAAACC TCTCTCCAGA CCTCAGCCAC    3720
ACGACTCTCT CTCCAGAACT CATTCAGAGA AACCTTTCCC CAGCCCTCGG TCAGATGCCC    3780
ATTTCTCCAG ACCTCAGCCA TACAACCCTT TCTCCAGACC TCAGCCATAC AACCCTTTCT    3840
TTAGACCTCA GCCAGACAAA CCTCTCTCCA GAACTCAGTC AGACAAACCT TTCCCCAGCC    3900
CTCGGTCAGA TGCCCCTTTC TCCAGACCTC AGCCATACAA CCCTTTCTCT AGACTTCAGC    3960
CAGACAAACC TCTCTCCAGA ACTCAGCCAT ATGACTCTCT CTCCAGAACT CAGTCAGACA    4020
AACCTTTCCC CAGCCCTTGG TCAGATGCCC ATTTCTCCAG ACCTCAGCCA TACAACCCTT    4080
TCTCTAGACT TCAGCCAGAC AAACCTCTCT CCAGAACTCA GTCAAACAAA CCTTTCCCCA    4140
GCCCTCGGTC AGATGCCCCT TTCTCCAGAC CCCAGCCATA CAACCCTTTC TCTAGACCTC    4200
AGCCAGACAA ACCTCTCTCC AGAACTCAGT CAGACAAACC TTTCCCCAGA CCTCAGTGAG    4260
ATGCCCCTCT TTGCAGATCT CAGTCAAATT CCCCTTACCC CAGACCTCGA CCAGATGACA    4320
CTTTCTCCAG ACCTTGGTGA GACAGATCTT TCCCCAAACT TTGGTCAGAT GTCCCTTTCC    4380
CCAGACCTCA GCCAGGTGAC TCTCTCTCCA GACATCAGTG ACACCACCCT TCTCCCGGAT    4440
CTCAGCCAGA TATCACCTCC TCCAGACCTT GATCAGATAT TCTACCCTTC TGAATCTAGT    4500
CAGTCATTGC TTCTTCAAGA ATTTAATGAG TCTTTTCCTT ATCCAGACCT TGGTCAGATG    4560
CCATCTCCTT CATCTCCTAC TCTCAATGAT ACTTTTCTAT CAAAGGAATT TAATCCACTG    4620
GTTATAGTGG GCCTCAGTAA AGATGGTACA GATTACATTG AGATCATTCC AAAGGAAGAG    4680
GTCCAGAGCA GTGAAGATGA CTATGCTGAA ATTGATTATG TGCCCTATGA TGACCCCTAC    4740
AAAACTGATG TTAGGACAAA CATCAACTCC TCCAGAGATC CTGACAACAT TGCAGCATGG    4800
TACCTCCGCA GCAACAATGG AAACAGAAGA AATTATTACA TTGCTGCTGA AGAAATATCC    4860
TGGGATTATT CAGAATTTGT ACAAAGGGAA ACAGATATTG AAGACTCTGA TGATATTCCA    4920
GAAGATACCA CATATAAGAA AGTAGTTTTT CGAAAGTACC TCGACAGCAC TTTTACCAAA    4980
CGTGATCCTC GAGGGGAGTA TGAAGAGCAT CTCGGAATTC TTGGTCCTAT TATCAGAGCT    5040
GAAGTGGATG ATGTTATCCA AGTTCGTTTT AAAAATTTAG CATCCAGACC GTATTCTCTA    5100
CATGCCCATG GACTTTCCTA TGAAAAATCA TCAGAGGGAA AGACTTATGA AGATGACTCT    5160
CCTGAATGGT TTAAGGAAGA TAATGCTGTT CAGCCAAATA GCAGTTATAC CTACGTATGG    5220
CATGCCACTG AGCGATCAGG GCCAGAAAGT CCTGGCTCTG CCTGTCGGGC TTGGGCCTAC    5280
TACTCAGCTG TGAACCCAGA AAAAGATATT CACTCAGGCT TGATAGGTCC CCTCCTAATC    5340
TGCCAAAAAG GAATACTACA TAAGGACAGC AACATGCCTG TGGACATGAG AGAATTTGTC    5400
TTACTATTTA TGACCTTTGA TGAAAAGAAG AGCTGGTACT ATGAAAAGAA GTCCCGAAGT    5460
TCTTGGGAGAC TCACATCCTC AGAAATGAAA AAATCCCATG AGTTTCACGC CATTAATGGG    5520
ATGATCTACA GCTTGCCTGG CCTGAAAATG TATGAGCAAG AGTGGGTGAG GTTACACCTG    5580
```

-continued

```
CTGAACATAG GCGGCTCCCA AGACATTCAC GTGGTTCACT TTCACGGCCA GACCTTGCTG      5640

GAAAATGGCA ATAAACAGCA CCAGTTAGGG GTCTGGCCCC TTCTGCCTGG TTCATTTAAA      5700

ACTCTTGAAA TGAAGGCATC AAAACCTGGC TGGTGGCTCC TAAACACAGA GGTTGGAGAA      5760

AACCAGAGAG CAGGGATGCA AACGCCATTT CTTATCATGG ACAGAGACTG TAGGATGCCA      5820

ATGGGACTAA GCACTGGTAT CATATCTGAT TCACAGATCA AGGCTTCAGA GTTTCTGGGT      5880

TACTGGGAGC CCAGATTAGC AAGATTAAAC AATGGTGGAT CTTATAATGC TTGGAGTGTA      5940

GAAAAACTTG CAGCAGAATT TGCCTCTAAA CCTTGGATCC AGGTGGACAT GCAAAAGGAA      6000

GTCATAATCA CAGGGATCCA GACCCAAGGT GCCAAACACT ACCTGAAGTC CTGCTATACC      6060

ACAGAGTTCT ATGTAGCTTA CAGTTCCAAC CAGATCAACT GGCAGATCTT CAAAGGGAAC      6120

AGCACAAGGA ATGTGATGTA TTTTAATGGC AATTCAGATG CCTCTACAAT AAAAGAGAAT      6180

CAGTTTGACC CACCTATTGT GGCTAGATAT ATTAGGATCT CTCCAACTCG AGCCTATAAC      6240

AGACCTACCC TTCGATTGGA ACTGCAAGGT TGTGAGGTAA ATGGATGTTC CACACCCCTG      6300

GGTATGGAAA ATGGAAAGAT AGAAAACAAG CAAATCACAG CTTCTTCGTT TAAGAAATCT      6360

TGGTGGGAG ATTACTGGGA ACCCTTCCGT GCCCGTCTGA ATGCCCAGGG ACGTGTGAAT       6420

GCCTGGCAAG CCAAGGCAAA CAACAATAAG CAGTGGCTAG AAATTGATCT ACTCAAGATC      6480

AAGAAGATAA CGGCAATTAT AACACAGGGC TGCAAGTCTC TGTCCTCTGA AATGTATGTA      6540

AAGAGCTATA CCATCCACTA CAGTGAGCAG GGAGTGGAAT GGAAACCATA CAGGCTGAAA      6600

TCCTCCATGG TGGACAAGAT TTTTGAAGGA AATACTAATA CCAAAGGACA TGTGAAGAAC      6660

TTTTTCAACC CCCCAATCAT TTCCAGGTTT ATCCGTGTCA TTCCTAAAAC ATGGAATCAA      6720

AGTATTACAC TTCGCCTGGA ACTCTTTGGC TGTGATATTT ACTAGAATTG AACATTCAAA      6780

AACCCCTGGA AGAGACTCTT TAAGACCTCA AACCATTTAG AATGGGCAAT GTATTTTACG      6840

CTGTGTTAAA TGTTAACAGT TTTCCACTAT TTCTCTTTCT TTTCTATTAG TGAATAAAAT      6900

TTTATACAA                                                             6909
```

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 2:

```
TGCTGACTAT GATTACCAGA                                                   20
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 3:

```
GAGTAACAGA TCACTAGGAG                                                   20
```

(2) INFORMATION FOR SEQ ID NO: 4:

-continued (i) SEQUENCE CHARACTERISTICS:
    (A) LENGTH: 20 base pairs
    (B) TYPE: nucleic acid
    (C) STRANDEDNESS: both
    (D) TOPOLOGY: unknown (ii) MOLECULE TYPE: cDNA (xi) SEQUENCE DESCRIPTION: SEQ ID NO: 4:

GCATTTACCC TCATGGAGTG                                                   20

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 5:

CAAGAGTAGT TATGCTCTCA GGCAC                                             25

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 6:

CACGTGGTTC ACTTTCACGG                                                   20

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 7:

TGTGGTATAG CAGGACTTCA GGTA                                              24

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: both
        (D) TOPOLOGY: unknown (ii) MOLECULE TYPE: cDNA (xi) SEQUENCE DESCRIPTION: SEQ ID NO: 8:

TATAAGATCC ACCATTGT                                                     18

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: both (D) TOPOLOGY: unknown (ii) MOLECULE TYPE: cDNA (xi) SEQUENCE DESCRIPTION: SEQ ID NO: 9:

TGCCCAGTGC TTAACAAGAC CA                                               22

(2) INFORMATION FOR SEQ ID NO: 10:

(i) SEQUENCE CHARACTERISTICS:
            (A) LENGTH: 20 base pairs
            (B) TYPE: nucleic acid
            (C) STRANDEDNESS: both
            (D) TOPOLOGY: unknown (ii) MOLECULE TYPE: cDNA (xi) SEQUENCE DESCRIPTION: SEQ ID NO: 10:

TGTTATCACA CTGGTGCTAA                                                  20

(2) INFORMATION FOR SEQ ID NO: 11:

(i) SEQUENCE CHARACTERISTICS:
            (A) LENGTH: 22 base pairs
            (B) TYPE: nucleic acid
            (C) STRANDEDNESS: both
            (D) TOPOLOGY: unknown (ii) MOLECULE TYPE: cDNA (xi) SEQUENCE DESCRIPTION: SEQ ID NO: 11:

GAGAGACATC GCCTCTGGGC TA                                               22

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: both
            (D) TOPOLOGY: unknown (ii) MOLECULE TYPE: cDNA (xi) SEQUENCE DESCRIPTION: SEQ ID NO: 12:

TGGACAGGCG AGGAATAC                                                    18

(2) INFORMATION FOR SEQ ID NO: 13:

(i) SEQUENCE CHARACTERISTICS:
            (A) LENGTH: 18 base pairs
            (B) TYPE: nucleic acid
            (C) STRANDEDNESS: both
            (D) TOPOLOGY: unknown (ii) MOLECULE TYPE: cDNA (xi) SEQUENCE DESCRIPTION: SEQ ID NO: 13:

TGGACAGGCA AGGAATAC                                                    18

(2) INFORMATION FOR SEQ ID NO: 14:

(i) SEQUENCE CHARACTERISTICS:
            (A) LENGTH: 149 base pairs
            (B) TYPE: nucleic acid
            (C) STRANDEDNESS: both
            (D) TOPOLOGY: unknown (ii) MOLECULE TYPE: cDNA -continued (xi) SEQUENCE DESCRIPTION: SEQ ID NO: 14:

```
GTATTTTGTC CTTGAAGTAA CCTTTCAGAA ATTCTGAGAA TTTCTTCTGG CTAGAACATG        60

TTAGGTCTCC TGGCTAAATA ATGGGGCATT TCCTTCAAGA GAACAGTAAT TGTCAAGTAG       120

TCCTTTTTAG CACCAGTGTG ATAACATTT                                         149
```

METHOD FOR SCREENING FOR THE PRESENCE OF GENETIC DEFECT ASSOCIATED WITH THROMBOSIS AND/OR POOR ANTICOAGULANT RESPONSE TO ACTIVATED PROTEIN C

RELATED APPLICATIONS

The present application is a continued prosecution application of U.S. application Ser. No. 09/165,019 filed Sep. 30, 1998, which is a divisional of commonly assigned U.S. patent application Ser. No. 08/454,353 entitled A Method for Screening for the Presence of Genetic Defect Associated with Thrombosis and/or Poor Anticoagulant Response to Activated Protein C filed Jun. 6, 1995, the disclosure of which is incorporated by reference as if set forth fully, which claims priority from European Patent Application Serial No. 94200377.3 filed Feb. 14, 1994.

The subject invention lies in the field of haemostasis and in particular is directed at the aspect of thrombosis. More particularly the invention is directed at a method for screening and diagnosis of thrombophilia, especially hereditary thrombophilia. The method according to the invention can then be used for determining the risk for thrombosis in individuals.

BACKGROUND TO THE INVENTION

Deep vein thrombosis is a common disease. Well established risk factors include recent surgery, malignant disorders, pregnancy and labour, long term immobilisation, and deficiency of one of the main inhibitors of the clotting system (Ref. 1). The main inhibitors are known to be protein C, protein S and antithrombin. The causes of deep vein thrombosis in many patients remain unclear. It has recently been established however that a poor anticoagulant response to activated protein C (APC) is present in several families with a hereditary tendency to venous thrombosis (Ref. 2).

The anticoagulant property of APC resides in its capacity to inactivate the activated cofactors Va and VIIIa by limited proteolysis (Ref. 3). This inactivation of cofactors Va and VIIIa results in reduction of the rate of formation of thrombin, the key enzyme of coagulation. In vitro, this effect can be visualised by adding APC to normal plasma and accordingly determining the effect thereof in a coagulation test, for example in a test determining the APTT (activated partial thromboplastin time). Activation of protein C occurs at the surface of endothelial cells via the thrombin-thrombomodulin complex (Ref. 27). Thrombomodulin is a membrane glycoprotein that can bind thrombin. By this binding thrombin loses the ability to convert fibrinogen to fibrin and the ability to activate blood platelets. In other words thrombin loses its coagulant properties and reduces its further own production (so-called negative feed-back) by activating protein C. In vivo (in the presence of calcium) the activation of protein C is almost completely dependent on the availability of thrombomodulin on the endothelium. APC is subsequently neutralized by formation of complexes with APC inhibitor (PCI) and $\alpha_1$ antitrypsin, which means that in normal conditions it remains only for a short time in the circulation and the anticoagulant effect remains generally locally expressed.

It was generally accepted that the inactivation of the cofactors Va and VIIIa by APC proceeds only optimally in the presence of $Ca^{2+}$, phospholipids and the APC cofactor protein S (Ref. 4, 28, 29). More recently this view was, however, challenged by the finding that in systems of purified proteins protein S has little cofactor activity to APC (Ref. 5, Ref. 6). A possible solution for this apparent discrepancy between the observations in vivo (thrombotic tendency in hereditary protein S deficiency) and in vitro (poor APC cofactor activity of protein S in systems of purified proteins) could be offered by the finding of Dahlbäck et al (Ref. 2) who reported patients with normal values for antithrombin activity, protein C (immunologically and functionally) and protein S (immunologically and functionally) without indications for abnormal plasminogen, abnormal fibrinogen or lupus anticoagulants, but with a reduced anticoagulant response to activated protein C. The latter was found with a new test developed by Dahlback (Ref. 2) in which he studies the response (coagulation time, APTT) of a plasma after in vitro addition of purified human APC. The addition of activated protein C to the plasma of these thrombotic patients did not result in the expected prolongation of the activated partial thromboplastin time (APTT). After postulating a number of mechanisms for this phenomenon only one was considered to provoke the poor anticoagulant response to APC, namely the existence of a hitherto unknown cofactor to APC that is deficient in these patients.

The following mechanisms have to date been rejected as being causes of the poor anticoagulant response to APC:
1. The presence of an auto antibody against APC
2. A fast acting protease inhibitor reacting with APC
3. A functional protein S deficiency
4. Mutations in the Factor V or Factor VIII gene Dahlbäck (Ref. 2, 7) postulated that in the families studied a hereditary shortage of a hereto unknown APC cofactor that purportedly works independently of protein S was the cause of APC resistance. Dahlbäck et al (Ref. 2) also described a test method for diagnosing the thrombo embolic disorders by addition of activated protein C to a patient sample containing coagulation factors followed by measurement of an enzyme activity that is influenced by the addition of APC in an international patent application WO93/10261. It is stated in the application of Dahlbäck et al that the experimental results presented indicated that the disorders in question are related to a hitherto unknown coagulation factor or factors or unknown interactions of known factors. The unknown factor is not Factor Va or VIIIa that is resistant to degradation by APC and neither is it an inhibitor of the immunoglobulin type of APC. Furthermore it is not related to protein S deficiency. Dahlbäck et al (Ref. 2) state that their invention is a method particularly useful for further diagnosis of thromboembolic diseases such as hereditary or non hereditary thrombophilia and for determining a risk for thrombosis in connection with pregnancy, taking anticonception pills, surgery etc. They describe their method as being characterized in that the coagulation system in a sample is activated, wholly or partly in a manner known per se and incubated with activated protein C, whereupon a substrate conversion reaction rate like clotting or conversion of a chromogenic substrate is determined. The conversion rate obtained is compared with values obtained for normal plasma samples. If the rate is enhanced it indicates that the individual from which the sample is derived may suffer from a clotting disease. The disease is not expressed by protein S deficiency or by formation of Factor Va or Factor VIIIa resistant to degradation by APC or by an inhibitor of the immunoglobulin type for APC. In the international application it is also stated by Dahlbäck et al that the data in the application indicated that the patient in question could not carry a defective Factor VIII/VIIIa in contrast to what they had previously stated in Thromb. Haemostas. 65, Abstract 39, 658 (1991), wherein addition of activated protein C to a plasma sample of a patient, and study of the effect produced was claimed to have illustrated a defective Factor VIIIa molecule not degraded by activated protein C. Furthermore in the international patent application the assay was used to directly measure the inhibition of Factors Va and VIIIa by APC. Using the Factor Xa based clotting assay described therein, the inhibition of patient Factor Va by APC was found to be normal suggesting that Factor Va in the patient's plasma was degraded in a normal fashion by exogeneously added APC.

Following the publication by Dahlbäck et al (Ref. 2) other groups started research in this area. In Blood Vol. 82, nr. 7, 1993 on pages 1989–1993 Griffin et al describe the results of APC resistance tests carried out among 25 venous thrombotic patients with no identifiable blood coagulation abnormality and 22 patients previously identified with heterozygous protein C or protein S deficiency. The APC induced prolongation of the activated partial thromboplastin time assay for these patients was compared with results for 35 normal subjects. The results showed that his new defect in antiocoagulant response to APC was surprisingly present in 52 to 64% of the 25 patients i.e. in the majority of previously undiagnosed thrombophilia cases. The deficiency was not present in 20 of 22 heterozygous protein C or protein S deficient patients. This suggested that the new factor is a risk factor independent of protein C or protein S deficiency. Mixing of normal blood plasma with each of two extremely defective plasmas (APC-induced prolongation of APTT<20 s) was performed and the APTT assays were made to assess the ability of normal plasma to correct the poor response of the defective plasmas. The results were similar to those of Dahlbäck et al (Ref. 2). This also suggested that normal plasma contains a factor which is missing from the defective patients plasmas. Values are given in the article for the net calculated prolongation in APTT, simply defined as an APTT value in the presence of APC minus the APTT value in the absence of APC. The article also describes the ratio of the APTT with APC to the APTT without APC and the fact that this parameter was compared to values for the APC induced APTT prolongation. This comparison indicated an excellent correlation between these parameters for the normals, with an extremely low APTT ratio value being indicative of abnormal patients. Therefore it followed that either the parameter of APC-induced APTT prolongation or the parameter of the ratio of APTT values with versus without APC or both parameters can be used as diagnostic parameter. None of these parameters seemed more useful for this purpose than the other according to the article. Furthermore in the article it was stated that the APC-induced prolongation of the APTT assay used was reminiscent of the assay involving APC-induced inactivation of endogenous Factor VIII in the plasmas of patients with lupus anticoagulant reported by Potzsch et al (Ref. 19) in Blood 80: 267a 1992 (Abstract)). Based on this latter assay it was reported in the Griffin et al article that plasma from lupus anticoagulant patients with thrombosis gave a poor response to APC and that patients with thrombosis could thereby be distinguished from those without thrombosis. Griffin et al speculated that auto-antibodies against the new hypothesized APC-cofactor could play a role in the risk of thrombosis among patients with lupus anticoagulants. It is further stated by them that it is tempting to speculate that an acquired deficiency of the new APC-cofactor could be associated with an acquired risk of thrombosis.

In the Lancet, Dec. 18, 1993, Vol. 342, on pages 1503–1506 Koster et al have elaborated further on the link between APC-resistance and thrombosis by describing how a population based case control study was undertaken to test the clinical importance of the abnormality in the coagulation system that is characterized by a poor antiocoagulant response to activated protein C (APC). From studies within families this poor response to APC appears to inherit as an autosomal dominant trait (Ref. 2, 7 and 47). Among patients referred to a coagulation unit because of unexplained thrombosis this abnormality was a major cause of thrombophilia with a prevalence of about 40% (Ref. 8 and 9). In the study described by Koster et al in the Lancet, Dec. 18, 1993, Vol. 342, pages 1503–1506, the clinical importance of this poor response to APC was investigated in unselected consecutive patients, aged less than 70 years, with a first objectively confirmed episode of deep vein thrombosis and without an underlying malignancy. The sensitivity of these patients plasma to APC was compared with that of matched healthy controls. The sensitivity of their plasma APTT to activated protein C (APC) was measured essentially as described by Dahlbäck et al (Ref. 2) using the reagents and reaction conditions previously developed for the protein S activity assay (Ref. 11). The results were expressed as APC sensitivity ratios (APC-SR) defined as the value of APTT (+APC) over the APTT (−APC). In the Koster et al article (Lancet, Dec. 18, 1993, Vol. 342, pages 1503–1506) it was stated that reduced levels of prothrombin and/or Factor X (<0.5 $\mu$/ml) will increase the APC-SR. For this reason the test cannot be used for the evaluation of plasma's of patients on oral anticoagulant treatment. In a series of 98 samples a good correlation was found between the APC-SR obtained with the test of Koster et al (Lancet, Dec. 18, 1993, Vol. 342, pages 1503–1506) and those obtained with the test developed by Chromogenix as described in WO 93/10261. A reference range for the APC sensitivity ratio was derived from the healthy control subjects. After logarithmic transformation of the data and exclusion of 10 subjects with values outside 3 standard deviations (SD) of the mean, the lower limit of normal was 2.17 (mean-1.96 SD). An inverse relation between the risk of thrombosis and the degree of response was found. The 21% prevalence of a poor response to APC among thrombosis patients and the odds ratio for thrombosis of 6.6 led to the conclusion that a poor response to APC could be considered a common and strong risk factor for deep vein thrombosis. It was even speculated that subjects with APC sensitivity ratios around 1.10 could be homozygous or double heterozygous, whereas subjects with APC sensitivity ratios around 1.50 could be heterozygous for the abnormality. The prevalence of the abnormality was 5% among the healthy control subjects. Because the distribution of the APC-SR was clearly bimodal Koster et al believe that subjects really had abnormal responses to APC rather than too low values within a normal range. The relation between risk of thrombosis and their response to APC seemed therefore not to follow the model of a simple single gene defect. Because the abnormality was found to be so prevalent in healthy subjects it was considered unlikely by Koster et al that the defect in itself is sufficient to cause thrombosis as is true also for protein C deficiency (Ref. 15, Ref. 16). An additional causal factor seems to be required for the development of thrombosis within a particular patient. These may be acquired factors and also as yet unknown genetic defects or variations. However once other causal factors are present poor APC response presents a strong risk of thrombosis as witnessed by its six to sevenfold increase of relative risk. It was stated in the article that the underlying defect of the poor response to APC remained to be clarified even though a dominantly autosomally inherited deficiency of a cofactor to activated protein C had been postulated (Ref. 7). While a poor response to APC appears to be 5 to 10 times as frequent as deficiencies of protein C, protein S or anti-thrombin it confers an approximately similar relative risk of thrombosis (Ref. 17 and 18) which according to Koster et al could make it worthwhile to test all patients with venous thrombosis for this abnormality.

In summary in the state of the art it was ascertained that a defect in the protein C anticoagulant pathway is linked to a relatively high risk of thrombosis. The poor anticoagulant response to activated protein C has been discussed in great detail, however the cause of the poor anticoagulant response to activated protein C remains unclear. A number of theories have been postulated, however the only one that has been accepted is the presence of an unknown cofactor for APC which is apparently deficient in a patient exhibiting a poor anticoagulant response to activated protein C. The identity of the postulated cofactor for APC is unknown. Furthermore current tests for detecting altered response to APC cannot be used on test persons already using anticoagulants.

DESCRIPTION OF THE INVENTION

Surprisingly the identity of the unidentified cofactor responsible for a poor anticoagulant protein C response has been found. It has been discovered that one of the mechanisms that had been rejected is in fact responsible for the defect in the protein C anticoagulant pathway in a majority of thrombophilic patients. The cause of the deficiency has been linked to the presence of a mutation in the nucleic acid material encoding Factor V or Factor VIII which upon expression is correlated to a decrease in the degree of inactivation by APC of said Factor V and/or of Factor Va, (the product of activation of said Factor V) or of said Factor VIII and/or of Factor VIIIa (the product of activation of said Factor VIII). The deficiency is therefore not the result of a mutation in an as yet unidentified cofactor for APC, but is in fact due to a defect in Factor V or Factor VIII or more particularly in the activation products thereof.

of a genetic defect associated with thrombosis and/or poor anticoagulant response to activated protein C (APC), said genetic defect being indicative of an increased risk of thrombosis or said genetic defect actually causing thrombosis in a patient, said method comprising determination of the presence of a mutation in the nucleic acid material encoding Factor V or factor VIII in a manner known per se, which mutation upon expression of the nucleic acid material is correlated to a decrease in the degree of inactivation by APC of said Factor V and/or of Factor Va (the product of activation of said Factor V) or of said Factor VIII and/or of Factor VIIIa (the product of activation of said Factor VIII) and/or comprising determination of a mutation present in the protein Factor V and/or Factor Va and/or present in the protein Factor VIII and/or Factor VIIIa by analysis of said Factor V and/or Factor Va or Factor VIII and/or Factor VIIIa or analysis of a proteolytic fragment of said Factor V and/or said Factor Va and/or Factor VIII and/or Factor VIIIa in a manner known per se, said mutation being correlated to a decrease in the degree of inactivation by APC of said Factor V and/or said Factor Va and/or Factor VIII and/or Factor VIIIa. In particular the method according to the invention is directed at a method wherein the mutation in the nucleic acid sequence encoding the Factor V and/or Factor VIII is located at the position within the part of the nucleic acid sequence encoding a binding site or a cleavage site of APC on Factor V and/or Va and/or Factor VIII and/or VIIIa and results in Factor V and/or Factor Va and/or Factor VIII and/or Factor VIIIa poorly inactivated by APC. There are known to be a number of binding and cleavage sites for APC in Factors V, VIII, Va and VIIIa. (see Table 1, refs. 34, 35, 36, 48, 49, 52 the article by Odegaard B & Mann K. G., in J. Biol. Chem. 262, 11233–11238 (1987) and the abstract by Kalafatis M., Haley P. E. & Mann K. G. in Blood 82, Suppl. 1, p. 58a, 1993).

TABLE 1

Cleavage and binding sites of activated protein C in Factor Va and Factor VIIIa

| Cleavage or binding site | Human factor V(a) sequence | Bovine factor V(a) sequence | Cleavage or Binding site | Human factor VIII or VIIIa |
|---|---|---|---|---|
| APC-cleavage | $R^{306}$-$N^{307}$ (ref. 51) | $R^{306}$-$N^{307}$ (ref. 48) | APC-cleavage | $R^{336}$-$M^{337}$ (ref. 49) |
| APC-cleavage | $R^{506}$-$G^{507}$ (ref. 51) | $R^{505}$-$G^{506}$ (ref. 48,50) | APC-cleavage | $R^{562}$-$G^{563}$ (ref. 49) |
| APC-cleavage | $R^{679}$-$K^{680}$ | $R^{662}$-$N^{663}$ (ref. 48,34) | APC-cleavage | $R^{740}$-$S^{741}$ (ref. 49) |
| APC-cleavage | ? | $R^{1752}$-$R^{1753}$ (ref. 48) | APC-cleavage | $H^{2009}$AGMSTLFIV (ref. 35) |
| APC-cleavage | ? | $R^{1753}$-$A^{1754}$ (ref. 48) | | |
| APC-cleavage | $R^{1861}$AGMQTPELI (ref. 35) | $R^{1852}$AGMQTPELI (ref. 35) | | |
| APC-cleavage | $K^{994}$ (ref. 52) | | | |

As was already indicated in the state of the art the link between a risk of thrombosis and the presence of APC-resistence had already been made and it had also been suggested that screening for such a deficiency would in fact be extremely helpful in diagnosing patients with an increased risk of thrombosis. As it is now known which factors carry the genetic defect responsible it has also now become possible to actually screen the population with methods other than the Chromogenix test for determining APC-resistance.

It has become possible to use DNA techniques or to use antibodies for determining the presence of mutant proteins when screening for the mutated Factor V or Factor VIII associated with resistance to APC. The subject invention is therefore directed at a method for screening for the presence Binding sites are not always cleavage sites. However, it is quite clear that any effect leading to reduced binding of APC to such a factor will also have an effect on the APC resistance of such a factor, as generally speaking the factor must be bound by APC before it can subsequently be cleaved by APC. The mutation affecting the binding and/or cleavage site can be present in the primary amino acid sequence of amino acids located at the binding site or can be due to a mutation elsewhere in the molecule resulting in a tertiary structure with a reduced affinity for APC binding and/or cleavage. As a number of sites for APC binding and/or cleavage have been clarified it is obviously easiest to screen for mutations at these locations rather than in the whole molecule. A number of cleavage sites of APC are known to be located on the heavy chains of the Factors V, Va, VIII and VIIIa preferably the mutation to be detected will be located at a position within the part of the nucleic acid sequence encoding a cleavage site of APC on the heavy chain.

The activation of Factors V and VIII can occur by thrombin Factor Xa, and in the case of factor V also by some snake venoms. For "activated by a particular factor" a person skilled in the art can also read "activated via a particular factor". The resulting activated factors differ slightly due to the manner in which they have been activated. It is therefore possible that a mutation resulting in reduced binding and/or cleavage by APC of Factor Va activated by thrombin will not result in reduced binding and/or cleavage by APC of Factor Va activated by Xa and vice versa. Factor V has the following domain structure A1A2/BA3C1C2, Factor Va that has been activated by Xa has the structure A1A2/B'A3C1C2, whereas Factor Va that has been activated by thrombin has the structure A1A2/A3C1C2. It is probable that the tertiary structure differs due to the variation in the structure of the light chains of the factors when they have been activated in different manners. In the example in this document it is illustrated that the particular mutation illustrated in fact only inhibited APC inactivation of Factor Va when activation was initiated via Xa and did not have an effect on APC inactivation of Factor Va that was activated via thrombin. This particular mutation was located on the heavy chain of Factor V and is therefore present in both Factor $V_a$ activated via thrombin and Factor Va activated via Xa but presumably does not exhibit the same effect in the two forms of activated Factor V due to a differing tertiary structure of the two forms of activated factors.

As in practice the inactivation by APC occurs on activated Factor V or activated Factor VIII the subject method is preferably directed at detection of a mutation resulting in a decrease of binding affinity for APC and/or a reduction in cleavage by APC on Factors Va or VIIIa. Generally speaking mutations present in Factors Va and Factors VIIIa will also be present on the Factor V or Factor VIII from which the activation product has been derived. Therefore analysis of the nucleic acid sequence encoding Factor V or Factor VIII will reveal mutations that can also be present in the activated Factors Va or VIIIa. The analysis according to the subject method can therefore be carried out at nucleic acid level e.g. at DNA and/or mRNA level of Factors V and VIII and at protein level on any of factors Va, VIIIa, V and VIII, or fragments derived from these.

Factor Va DNA has been cloned from HepG2 cells (Ref. 20) and human fetal liver (Ref. 21 and 22). The complete Factor V amino acid sequence is known (refs. 20, 23) also the organisation of the factor V gene has been elucidated (Ref. 23). Shen et al (The Journal of Immunology, Vol. 150, 2992–3001, No. 7, Apr. 1, 1993) have described how they found a cellular source of human Factor V. They identified Factor V mRNA in human lymphoid cells by using reverse transcription followed by the polymerase chain reaction (RT-PCR). The results from the PCR were confirmed by independent cloning of Factor V cDNA from a T-cell cDNA library. The sequence of the Factor V cDNA was virtually identical to hepatic Factor V mRNA. A limited span of mRNA encoding part of the connecting region of the Factor V protein was found to contain nucleotide polymorphisms based on 6 nucleotide substitutions. Shen et al described that the amplified F7/F8 Factor V cDNA fragment, present in 14 independent clones derived after amplification, comprised 6 nucleotide base substitutions. 2 Substitutions were of thymine to cytosine and from cytosine to thymine at positions 2209 and 2236 respectively that were silent mutations. Four were guanine to adenine base substitutions that also resulted in a silent mutation at position 2302 and also amino acid changes from arginine to lysine at position 2573, from arginine to histidine at position 2595 and from glutamic acid to lysine at position 2773. These deduced amino acid changes are described in the article as conservative substitutions that did not significantly affect Factor V function. Half of the clones (7 of 14) in addition exhibited an adenine to guanine substitution at position 2290, another silent substitution which abolished the EcoR1 site. None of these mutations have been associated with a decreased affinity for APC binding or cleavage.

In the article by Shen et al it is illustrated that Factor V mRNA can be recovered from human lymphoid cells in sufficient amounts to carry out polymerase chain reactions for example. With this information a person skilled in the art will have no difficulty in retrieving nucleic acid from humans in a sufficient amount to carry out the method according to the subject invention. In the Shen et al article a number of oligonucleotides are presented which can be used in nucleic acid amplification of human Factor V nucleic acid.

Bruce Odegaard and Mann (The Journal of Biological Chemistry, Vol. 262, No. 23, August 15, pp. 11233–11238, 1987) described for both Factor V and Va that cleavage of Factor V by thrombin results in a heavy chain (D chain) of $M_r$=94.000 and a light chain (E chain) of $M_r$=74.000. Each chain in itself is susceptible to proteolysis by activated protein C and by Factor Xa. Cleavage of the E chain by either activated protein C or Factor Xa yields two major fragments $M_r$=30.000 and $M_r$=48.000. They also indicated that the activated protein C and Factor Xa cleave the E chain at the same position. The activated protein C cleavage of the D chain yields two products $M_r$=70.000 and $M_r$=24.000. The $M_r$=70.000 fragment has the same $NH_2$-terminal sequence as intact D chain, the $M_r$=24.000 fragment does not. They illustrated that the cleavage of D chain by activated protein C was responsible for the partial inactivation of Factor Va. Evidence that the inactivation of Factor Va is associated with cleavage of its heavy chain, as the light chain is cleaved at a slower rate, is also present in Refs. 10, 12, 12, 14, and 48.

Odegaard and Mann also disclosed that there is a large deal of similarity between Factor Va and Factor VIIIa. Factor VIIIa is another cofactor of the clotting cascade whose activity is regulated by proteolysis. Factors VIIIa and Va have many similar structural and functional characteristics. Both are produced from a large procofactor through cleavage by thrombin or factor Xa, both are about the same size and consist of a heavy chain and a light chain. Both contribute greatly to the activity of a proteolytic complex while not exhibiting proteolytic activity on their own, and both are inactivated by activated protein C. Underlying this commonality is also an apparent homology of primary structure (Ref. 24, 25 and 26). They also themselves identified further sequence homology between Factors V and VIII. In particular they stated there are clearly segments of sequence homology between bovine Factor V and human Factor VIII at positions in the Factor VIII molecule that correspond reasonably well to the positions in the Factor V molecule at which cleavages occur. The effect illustrated by us for human Factor V (in example 1) can due to the equivalence of Factor V and Factor VIII in certain aspects also be expected concomitantly for Factors VIII and/or VIIIa. Odegaard and Mann also indicated that even when no heavy chain remained after cleavage of Factor Va by APC there remained residual cofactor activity. This indicated that the inactivation of Factor Va was a more complex event than simply the cleavage of a single bond, which makes the illustration of the examples of this document that a mutation in an APC binding and/or cleavage site of a Factor V molecule is in fact sufficient to cause a reduction in affinity for inactivation by APC even more surprising. For Factor VIII the APC cleavage sites have been postulated at Arg 562, Arg 336 and Arg 740 (Ref. 49) and the APC binding site in the A3 domain on residues 2009–2018 (Refs. 35, 36) (see also Table 1).

The method according to the invention is directed at detecting one or more mutations at one or more of the cleavage and/or binding sites for APC of Factor V and/or Factor Va or at Factor VIII and/or VIIIa at either nucleic acid or protein level or both. In particular the APC binding and/or cleavage sites located on the heavy chain of the protein or on nucleic acid encoding the heavy chain are considered relevant.

Kalafatis et al (Blood 82, Suppl. 1, p. 58A, 1993) illustrated that membrane bound human Factor Va was inactivated by activated protein C after cleavage of the heavy chain at Arg 506 and Arg 306. They illustrated that the cleavage pattern of the heavy chain of human Factor Va was dependent on the presence or absence of PCPS vesicles. In the absence of a membrane surface or in the presence of phospholipid vesicles exclusively composed of PC, cleavage resulted in a fragment comprising residues 1–506 and a fragment starting with residue 507, which is further cleaved by APC at the COOH-terminus. In contrast, in the presence of PCPS vesicles the complete loss of activity is correlated with the cleavage of the $M_r$=75.000 fragment and the appearance of $M_r$=40.000 and $M_r$=30.000 fragments. The $M_r$=30.000 fragment corresponds to residues 307 to 506 demonstrating cleavage by APC at Arg 306. No cleavage of the light chain of the cofactor is observed in the presence as well as in the absence of PCPS vesicles after incubation with APC. Thus, a specific APC cleavage site is exposed when the cofactor is bound to PCPS. The presence of a membrane is essential for complete inactivation of human Factor Va by APC and cleavage at Arg 506 only partially inactivates the cofactor and cleavage at Arg 306 is anionic lipid dependent and is required for the complete inactivation of human Factor Va. Recently, similar data have been published for the inactivation of bovine factor Va by APC (Ref. 48). It is clear from the state of the art that there are thus at least two potential cleavage sites in human Factor Va for APC. Kalafatis et al have also detected an additional APC cleavage site at lysine 994 of human factor V (ref 52). Therefore the method according to the invention is directed at detecting mutations at one or more of these cleavage sites for APC in Factor V and/or Va at either nucleic acid or protein level, or both. The cleavage sites for APC are located at Arg 506 and Arg 306 on the heavy chain. A further site has been found to be present at amino acid Arg 679 and Lys 994.

In view of the above the method according to the invention for screening for the presence of a genetic defect associated with thrombosis and/or poor anticoagulant response to activated protein C (APC) said genetic defect being indicative of an increase risk of thrombosis or said genetic defect actually causing thrombosis in a patient, said method comprising determination of the presence of a mutation in the nucleic acid material encoding Factor V in a manner known per se which mutation upon the expression of the nucleic acid material is correlated to a decrease in the degree of inactivation of APC of said Factor V and/or of Factor Va is of particular interest when the Factor V has been derived from Factor V activated by Xa.

In particular the method according to the invention is directed at determination of the mutation in a nucleic acid sequence encoding human Factor V or Va with a mutated amino acid sequence comprising an altered amino acid at a position corresponding to amino acid 506 of the sequence of plasma Factor V (Ref. 21). In particular when the above-mentioned mutation is a mutation whereby the amino acid arginine has been replaced by the amino acid glutamine at amino acid 506 of the sequence of plasma Factor V. This is in particular the case when the second nucleotide of the codon for the amino acid corresponding to amino acid 506, nucleotide G is mutated. In particular when the nucleotide G is mutated to A at the position corresponding to the second nucleotide of the codon for the amino acid corresponding to amino acid 506 of the sequence of plasma Factor V.

As is apparent from the Examples the subject invention is also directed at a method for determining whether a test person is homozygous or heterozygous for a mutation in Factor V and/or Factor Va or Factor VIII and/or Factor VIIIa comprising carrying out a method known per se for determining whether a defect is present in anticoagulant response to APC, subsequently followed by determination of a value of a parameter known to be useful for diagnosis of the defect such as the (APTT+APC) over (APTT−APC) value and comparing the value obtained with a value obtained in the same manner for a sample for a normal individual or from an individual known to be homozygotic or heterozygotic, thereby establishing whether the test person is homozygotic or heterozygotic for a defect in anticoagulant response to APC, in combination with any known method for determining the presence and optionally the nature of a mutation in Factor V and/or Va or Factor VIII and/or Factor VIIIa in particular in the embodiment illustrated in Example 1 and any equivalent embodiments of said Example for other mutations in Factors V, Va, VIII and/or VIIIa resulting in altered anticoagulant response to APC, most particularly due to a mutation in an APC binding and/or cleavage site.

The method according to the invention can be accomplished by detecting the mutation by carrying out a nucleic acid target amplification reaction. Such target amplification reactions are well known to a person skilled in the art. It is required to use one or more primers specific to recognize and hybridize to stretches of nucleic acid adjacent to the 5' and 3' end of the stretch of nucleic acid in which the mutation can be located, said hybridisation being to a degree sufficient for amplification of the stretch of nucleic acid in which the mutation can be located. The stringency of hybridisation required is also known to a person skilled in the art of target amplification of nucleic acid. There are a number of target amplification reactions that are generally carried out in the state of the art comprising NASBA (Nucleic Acid Sequence Based Amplification) PCR (Polymerase Chain Reaction), LCR (Ligase Chain Reaction) and RCR (Repair Chain Reaction). For PCR target amplification methods the Amplicor$^R$ reaction kits are commercially available. It is also possible to use a primer sufficiently specific to recognize and hybridize to the stretch of nucleic acids in which the mutation itself can be located. An alternative amplification method comprises branch chain amplification as commercially exploited by Chiron wherein the probe rather than the target is amplified.

After amplification of the nucleic acid, analysis of the amplified nucleic acid in a manner known per se for detecting the presence and optionally the nature of the mutation is to be carried out in the method according to the invention.

It is also possible to determine the mutation without amplification of the nucleic acid material. There are a number of techniques known to a person skilled in the art that were used before the target amplification reaction was developed for determining the presence of mutations on nucleic acid and these can all be used in various embodiments of the method according to the invention. For example the mutation to be determined can be detected by a hybridisation reaction to at least one nucleic acid sequence sufficiently specific to hybridise to at least part of the nucleic acid sequence encoding the factor to be analysed when using normal to stringent hybridisation conditions e.g. blotting techniques followed by analysis of the nucleic acid thus isolated in a manner known per se for detecting the presence and optionally the nature of the mutation.

The detection of the presence and optionally the nature of the mutation can occur by subjecting the nucleic acid thus isolated to sequence analysis by using for example the Sanger sequence reaction to ascertain the nucleic acid sequence and subsequently to compare the results of this sequencing with the sequence known for the non-mutated factor. It is also possible to subject the nucleic acid sequence isolated to a further hybridisation test. The further hybridisation test being carried out with a stretch of nucleic acid material with a corresponding complementary sequence of sufficient length and specificity to at least hybridize to a fragment of the nucleic acid material comprising the mutation to detect the presence and optionally the nature of the mutation. The first hybridisation step merely isolates nucleic acid encoding the factor whether this is mutated or not and the second hybridisation step actually comprises hybridising the isolated sequence to the complementary sequence of the actual mutated nucleic acid sequence one wishes to ascertain in order to determine the presence or absence of said mutation on the isolated nucleic acid material. This latter hybridisation reaction should be carried out under stringent conditions for reliable results whilst the other hybridisation steps can be carried out under normal to stringent conditions. Thus two classical methods for determining the presence of a mutation on a particular nucleic acid are hereby illustrated and it will be obvious to a person skilled in the art that a number of known techniques can be used. In various standard books for molecular biology such techniques are amply illustrated for example in Sambrook, J., Fritsch, E. F., Maniatis, T. Molecular Cloning: a Laboratory Manual. (Cold Spring harbor Laboratory Press, cold Spring Harbor, N.Y. 1989.

It is also possible to analyse the amplified nucleic acid material obtained in the screening method according to the invention by using subsequent analysis tests using sequencing reactions or hybridisation to a corresponding complementary sequence of sufficient length and specificity to at least hybridize to a fragment of the nucleic acid material comprising the mutation to detect the presence and optionally the nature of the mutation as was illustrated above for analysis of isolated nucleic acid material that had not been subjected to an amplification reaction.

In particular for analysis of the presence of mutations in Factor V the isolated and/or amplified nucleic acid material can be subjected to a hybridisation test to a stretch of nucleic acid material selected from sequences with sequence numbers 12 and 13 of the sequence listing. For example an extremely suitable primer or nucleic acid sequence for hybridisation comprises at least a part of intron 10 of the nucleic acid sequence encoding human Factor V or a derivative thereof capable of hybridizing to said part of intron 10 under stringent conditions. Such a derivative will preferably be more than 90% homologous to the corresponding part of intron 10. The nucleic acid sequence of human Factor V is known and in sequence number 1 of the sequence listing the nucleic acid sequence encoding human Factor V is illustrated. The sequence is derived from Ref. 21. Using the nucleic acid sequence for hybridisation comprising at least a part of intron 10 it is quite simple to isolate and/or amplify and/or subsequently detect a mutation present in nucleic acid encoding Factor V, in particular of nucleic acid encoding an APC binding and/or cleavage site. It is in particular suitable to detect a mutation located on the heavy chain (see sequences 10, 14). Further, primers of nucleic acid sequences for hybridisation and/or amplification purposes can be selected from sequences with sequence listing numbers 2–11 of the sequence listing. As is already indicated above a number of other oligonucleotide primers are also known from the state of the art. It is also possible to use these primers for amplification purposes or hybridisation reactions to isolate the nucleic acid encoding Factor V and/or Va. It lies within the reach of a person skilled in the art to select oligonucleotide sequences best suited to isolate and/or amplify and/or determine the presence and nature of the mutation he is screening for in a method according to the invention as the sequence encoding the normal factor is known, as is a sequence for a mutated factor.

In the method according to the invention, in particular when the nucleic acid to be analysed has been subjected to target amplification, the isolated and/or amplified and/or hybridised nucleic acid material is subjected to sequence analysis and the sequence is then compared to the nucleic acid sequence of the corresponding non-mutated factor. It is also possible to analyse the amplified or isolated and/or hybridised nucleic acid material through restriction fragment analysis. In particular for the mutation illustrated in the example with Factor V that is mutated, the enzyme that can be used in Mn1 I. Naturally the restriction enzyme one can use for a restriction fragment analysis depends on the nature of the mutation to be detected and the location thereof. Determination hereof lies within the reach of a person skilled in the art without involving further inventive step, merely routine experimentation not placing an undue burden on a person skilled in the art.

As stated above the method according to the invention can also be carried out by analysing the protein rather than the nucleic acid sequence encoding the protein. In particular this is a useful embodiment of the invention when the mutation in the protein is located at a position within the part of the amino acid sequence providing a binding and/or a cleavage site of APC on Factor V or Va and results in Factor V and/or Factor Va poorly inactivated by APC or is located on the part of the nucleic acid sequence providing a binding and/or a cleavage site of APC of Factor VIII or VIIIa and results in Factor VIII and/or Factor VIIIa poorly inactivated by APC.

As stated above the presence of a mutation within the part of the amino acid sequence providing a cleavage site of APC on Factor V, Va, Factor VIII or VIIIa is a mutation that will quite clearly lead to an altered resistance of the mutated factor to inactivation by APC and therefore determination of such a mutation is a preferred embodiment of the method according to the invention. As already indicated in the state of the art, inactivation of Factor Va or Factor VIIIa generally ensues when APC cleaves the heavy chain of the factor. Therefore, detection of a mutation in such a cleavage site resulting in an amendment of a degree of cleavage of the mutated factor is a preferred embodiment of the invention. When analysing the protein for a mutation it is not only the primary amino acid sequence of the cleavage site itself that is relevant, but also the tertiary structure of the protein can be distorted due to a mutation somewhere in the primary sequence not immediately associated with the binding and/or cleavage site. It is well known that mutations located quite a long way away from the actual binding site or cleavage site of a protein can exhibit a large effect on the tertiary structure of the protein thereby also abolishing or reducing binding to said protein in this instance binding by APC. Therefore the method according to the subject invention is not only directed at detection of mutations in the primary nucleic acid sequence of the cleavage and/or binding sites for APC but also at detection of mutations resulting in a mutated factor having an altered tertiary structure resulting in reduced binding and/or cleavage of the factor by APC.

As the Factors V and VIII can both be activated by different mechanisms and the resulting activated factors are known to differ both in tertiary structure from the factors from which they have been derived it is apparent that the mutation in Factor V or Factor VIII could have no influence on the APC binding and/or cleavage sites of said molecules but could have an effect on those of the activated factors or vice versa. Nevertheless the mutation in primary amino acid sequence responsible for the altered binding and/or cleavage of the activated Factor V or VIII will also be present on Factor V or Factor VIII. When the detection of the mutated protein occurs by using a specific antibody it is possible to use an antibody specifically directed against the activated factor comprising the mutation for detection of the presence and optionally the nature of the mutation. Alternatively it is also possible to proteolytically cleave the protein to be analysed, thereby obtaining linear or partially linear structures making it possible to use antibodies specific for the mutation in the primary amino acid sequence of Factor V and/or Va or Factor VIII and/or VIIIa. Thus the detection method of the mutation need not be restricted to analysis of the activated factors but can in fact also occur on Factor V or Factor VIII that have not yet been activated.

If the mutation is present in a binding and/or cleavage site for APC then treatment of Factor V, Va, VIII, VIIIa with APC followed by analysis of the fragments in a manner known per se should reveal different fragments than when the Factor is normal.

For instance in the case of Factor V a mutation at amino acid 506 prevents cleavage and/or binding of APC there. Treatment with activated APC will thus result in cleavage at sites 306, 679 and 994, providing one fragment of aa 307–aa 679 and three other fragments comprising a sequence of 1–306, 680–994 and 995-terminus. The fragment of interest being 307–679. A normal Factor V will not comprise this fragment but will comprise two other fragments i.e. aa 307–506 and aa 507–679 due to the active cleavage site at aa 506. Thus detection of the aa 307–aa 679 indicates the presence of a mutated APC site at amino acid 506.

An extremely elegant test could comprise subjecting the Factor V after treatment with APC to the presence of 2 antibodies. Such a treatment with APC naturally occurs during preparation of serum. One antibody in the test being specific for a site of the protein upstream of amino acid 506, said site being located downstream of aa 306, the most adjacent cleavage site upstream of aa 506. The second antibody being specific for a site of the protein downstream of amino acid 506, said site being located upstream of aa 679, the most adjacent cleavage site for APC downstream from aa 506. The test comprises detection of a fragment detected by both antibodies. Such a test can be a sandwich immunoaassay. Preferably one antibody will be immobilized or can be immobilized and the other antibody will be provided with a detectable marker in a manner known per se for a person skilled in the art of immuno-assays. Use of an antibody specifically recognizing a part of the fragment 307–506 in such a test falls within the scope of the invention. An antibody specifically recognizing a part of the fragment 507–679 as such and the use thereof in a test as just described falls within the scope of the invention. Preferably the antibodies will be monoclonal antibodies. A suitable test can be carried out to detect a mutation in the APC cleavage site located at Arg 306 in an analogous manner using 2 antibodies, one specific for a part of fragment 1–306 and one specific for a part of fragment 307–506. Use of an antibody specifically recognizing a part of the fragment 307–506 in such a test falls within the scope of the invention. An antibody specifically recognizing a part of the fragment 1–306 as such and the use thereof in a test as just described falls within the scope of the invention. A test can also be carried out in an analogous manner to that described above for detection of a mutation in the APC cleavage site located at amino acid 679. for this mutation one antibody specific for a part of the fragment 507–679 is required and one antibody specific for a part of the fragment downstream of amino acid 680 is required. Use of an antibody specifically recognizing a part of the fragment 507–679 in such a test falls within the scope of the invention. An antibody specifically recognizing a part of the fragment 507–569 and an antibody specifically recognizing a part of the fragment 570–994 as such and the use of one or more of these antibodies in a test analogous to that described above falls within the scope of the invention. Analogously a test can be described for detection of a mutation at the APC cleavage site at lysine 994. The fragments 994-terminus and 680–994 are the relevant fragments, as are the antibodies capable of recognising them.

In general terms the test for a mutation in Factor V, Va, VIII or VIIIa can comprise use of 2 antibodies in an immunoassay in a manner known per se to detect the presence or absence of a mutation decreasing or inhibiting cleavage by APC at a particular APC cleavage site, wherein one antibody recognizes a fragment upstream of said APC cleavage site, the second antibody recognizes a fragment downstream of said APC cleavage site, and no other APC cleavage sites are located between the part of the Factor either antibody recognizes and the particular APC cleavage site for which the presence or absence of a mutation has to be determined. The various embodiments following from this principal of mutation detection will be obvious to a person skilled in the art of immunoassays. It will thus be obvious for example that one or more additional proteases can be used in combination with APC, said APC having to be added or already being present in the sample depending on which type of sample is used. The additional protease or protease being selected such that the absence of the active APC cleavage site to be detected on the Factor results in the binding of both antibodies to the proteolytic fragment comprising the inactive APC cleavage site, whereas the presence of the active APC cleavage site to be detected results in proteolytic fragments such that the antibodies cannot both bind to a proteolytic fragment. This is most simply arrived at the selection of one or more protease resulting in cleavage of the Factor upstream and downstream of the APC cleavage site to be analysed and one of the two antibodies recognising a part of the fragment upstream of the APC cleavage site to be determined and downstream of the location the protease cleaves upstream of the APC cleavage site and the other of the two antibodies recognising a part of the fragment downstream of the APC cleavage site to be determined and upstream of the location the protease cleaves downstream of the APC cleavage site and the protease or proteases cleaving the Factor such that their cleavage sites are located between the APC cleavage site to be determined and the adjacent APC cleavage site as present on a non mutated Factor. In yet a further embodiment one can apply in lieu of APC a protease capable of cleavage of the mutated APC cleavage site but not of the non mutated APC cleavage site or vice versa. Once the nature of the mutation to be determined is ascertained it is a matter of routine experimentation for a person skilled in the art to screen the recognition sites known for proteases for a suitable protease.

A further possibility for detection of the mutation lies in the older technique of amino acid sequence analysis. Once the amino acid sequence of the non-mutated factor is known it is quite simple to determine the amino acid sequence of the factor to be analysed and compared that sequence to the known sequence of the corresponding non-mutated factor. However, using antibodies is a simple and efficient way to analyse proteins for the presence of mutations, for example using ELISA's or RIA's or a variety of other immunological tests known to a person skilled in the art.

It is also possible that the activated forms of Factor V and Factor VIII only exhibit a reduction in APC binding and/or cleavage when activated by one particular mechanism. This is illustrated in Example 1 for Factor V, wherein the activated form that has been activated using thrombin does not exhibit any altered binding and/or cleavage capacity for APC whereas the activated form that has been activated by Factor Xa does exhibit a reduction in the binding and/or cleavage by APC. However, as stated above, it is of course possible to detect the presence of the mutation on either Factor V, Factor Va activated by thrombin or Factor Va activated by Xa, regardless of whether the effect of the mutation only occurs in one of the activated forms.

As is illustrated in Example 1 a specific mutation in Factor V has been discovered that is representative for a very large percentage of patients exhibiting thrombophilia without the cause thereof having been previously determined. This concerned a mutation of the amino acid at a position corresponding to amino acid 506 of the amino acid sequence of plasma Factor V (as disclosed in Ref. 21) and therefore a method wherein the mutation of amino acid 506 can be determined forms a preferred embodiment of the invention. In general a method wherein the mutation to be detected comprises an alteration of the arginine amino acid located in an APC cleavage site, in particular on a heavy chain of Factor V(a) and/or Factor VIII(a) is an embodiment of the subject method that can be suitably carried out.

For detecting the mutation one can use a specific antibody capable of binding to the mutant protein V and/or Va or of binding to a linear proteolytic fragment of the mutant protein Factor V and/or Va, said antibody having a lower binding affinity for the non-mutated protein or for the corresponding proteolytic fragment of the non-mutated protein. The method with antibodies can also be used for protein Factor VIII and/or VIIIa and linear proteolytic fragments of said mutant protein Factor VIII and/or VIII*a*.

It is also possible as an alternative to use an antibody capable of binding to a protein Factor V and/or Va or a protein Factor VIII and/or Factor VIIIa, said protein not exhibiting a decrease in the degree of inactivation by APC, said antibody having a lower binding affinity for the corresponding factor and/or for the proteolytic fragment thereof comprising a mutation resulting in the mutated protein exhibiting a decrease in the degree of inactivation by APC. In this instance a test can be developed whereby non-binding of the antibody to the isolated protein or proteolytic fragment is illustrative of the presence of a mutation. The invention is not only directed at methods using antibodies as described above but is also directed at the antibodies themselves.

In the method according to the invention it is possible to first screen a sample for an altered coagulation time upon addition of APC in comparison to that of a normal plasma standard, followed by analysis of the nucleic acid sequence encoding Factor V or Factor VIII and/or of amino acid sequence of Factor V, Va, VIII or VIIIa and/or analysis of Factor V, Va, VIII or VIIIa itself once the sample is diagnosed as exhibiting altered APC resistance in comparison to the standard. It is also possible to immediately subject a sample to analysis for the presence of a specific mutation, for example for the mutation in Factor V illustrated in the following Examples. The methods to be used will depend on the circumstances of the case and also the objective of the test. For example when screening a large population the cheapest method to be used will be preferred. In some instances the mutation to be detected will be difficult to determine using antibodies and then use of nucleic acid sequences or restriction fragment analysis can be preferred. Also if the enzyme to be used for a restriction fragment test is inexpensive then carrying out such a test is very simple and cheap to carry out and will obviously be suitable. The invention is therefore also directed at use of a test for determining whether a sample exhibits altered binding and/or cleavage by APC in comparison to a sample comprising normal Factor V and/or Factor VIII and/or Factor VIII$_a$ and/or Factor Va, followed by further analysis of the mutation causing this alteration in a manner elucidated above.

Another aspect of the invention lies in the detection of a mutation in Factor V, Va, VIII or VIIIa being homozygous or heterozygous in the test person. This can be carried out using the test protocol as described by Koster et al in Lancet, Dec. 18, 1993, Vol. 34 for determining whether a test person exhibits APC resistance. Basically Koster describes use of 50 μl undiluted plasma incubated with 50 μl APTT reagent (Cephotest®, batch 103029) for 360 seconds at 37° C. before clot formation was started either with 50 μl of a reagent containing 33 mM CaCl$_2$, 25 mM Tris (pH 7.5), 50 mM NaCl and 0.05% ovalbumin (APTT-APC) or with 50 μl of the same reagent also containing 2.0 μg/ml human APC and 0.6% glycerol (APTT+APC). He expressed his results as APC sensitivity ratio's (APC-SR) defined as the ratio of APTT (+APC) and APTT (−APC). Under these conditions the APC-SR is achieved for normal plasma. Reduced levels of prothrombin and/or Factor X (<0.5 U/ml) will increase the APC-SR. This method therefore cannot be used for evaluation of patients on oral anticoagulant treatment. Koster further stated that with this test he found a good correlation between his results and those obtained using the Chromogenix assay (Pearson correlation coefficient 0.54) discussed in the introduction. Surprisingly we discovered that the Koster test when applied for assessing whether a subject is heterozygous or homozygous for mutation in Factor V detects abnormals a lot better than the Chromogenix test which misses approximately half the heterozygotes. FIG. 14 is the Koster test and FIG. 11 is the Chromogenix test. We carried out tests twice during the Koster method and the Chromogenix test as commercially available on samples from a random selection of individuals genotyped as 1691 GG (normals) or 1691 AG (heterozygotes). In the Chromogenix test there was a great deal of overlap between the sensitivity ratios obtained in normals and heterozygotes, so that more than 50% of the heterozygotes could not be identified as APC resistant with the Chromogenix test. We therefore have found an additional test suitable for determining whether a test person is abnormal or normal for Factor V mutation resulting in APC resistance. Whereas previously the Koster test was merely postulated to be useful to determine whether a test person is normal or abnormal with regard to APC resistance in general we have now discovered it in fact detects Factor V mutation leading to APC resistance and in addition it does to a much higher degree of reliability than the Chromogenix test can. A value of less than 0.84 is abnormal in our test and no overlap occurs between normal subjects and heterozygotes. This is a significant improvement over the Chromogenix test. We believe the improvement is due to the use of a different activator and more importantly the use of a different calcium concentration than in the Chromogenix test. The improved test comprises applying a calcium concentration of more than 25 mM $CaCl_2$ in the sample. Preferably less than 45 mM, more preferably 30–40 mM, in particular 31–35 mM. This higher concentration probably neutralizes citrate in the sample to a better degree than in the Chromogenix formula. A further improvement lies in the use of Cephotest reagent as activator. The method is further analogous to the Chromogenix test and must be considered a considerable improvement thereof. When values obtained for the APC sensitivity ration have been normalised (see Example 1) a value below 0.84 is indicative of abnormally and a value above 0.084 is indicative of normally regarding APC resistance, in particular related to Factor V mutation. For homozygotes deter,omatopm a value below 0.50 must be registered, with heterozygotes exhibiting values between 0.50 and 0.70. This improved method however is not applicable on patients that have been subjected to treatment with anticoagulant.

In the example the mutation that was detected was the G→A mutation at the codon for amino acid 506 of Factor V. The frequency of occurrence of the mutation and the associated high risk of thrombosis means that determination whether a test person is homozygous or heterozygous is extremely relevant when assessing the risks for parents for passing on the mutated factor to their progency. In Example 2 we illustrate that the presence of a mutation in Factor V, in particular the G→A mutation in fact is a risk factor for developing thrombosis. Moreover the preliminary observation that 6% of the patients with a first myocardial infarction is a carrier of the 1691 G-A mutation, might indicate that this mutation is also a mild risk factor for arterial thrombosis (relative risk 1,5–2,0). The timely detection of an increased risk for heart attack can lead to a person adjusting like style and taking precautions to prevent such an event. The importance regarding venous thrombosis has already been discussed in the introduction.

The invention is also directed at kits comprising the elements necessary for carrying out the method according to the invention in all the embodiments illustrated. This comprises for example test kits comprising one or more of the specific antibodies described above, in particular the parts of antibodies described recognizing sites between APC cleavage and/or binding sites and/or comprising one or more probes or primers or pairs of primers for target amplification reactions and/or hybridisation reactions as described above. Specifically the invention is directed at a kit comprising a primer or primers for amplifying the nucleic acid sequence comprising the mutation of the nucleic acid sequence coding for amino acid 506 of Factor V and/or Factor Va. The kit can comprise primers and/or antibodies for the detection of one particular mutation or for a number of mutations. Preferably the kit will comprise the components necessary to detect the major mutations leading to a decrease and/or abolition of binding and/or cleavage by APC that are prevalent in specific populations.

EXAMLE 1

Recently a poor anticoagulant response to APC ("APC-resistance" (Ref. 2)) was found in the plasma of 21% of unselected consecutive patients with thrombosis (Lancet, Dec. 18, 1993, Vol. 342, pp. 1503–1506, T. Koster et al) and about 50% of selected patients with a personal or family history of thrombosis (Ref. 8 and Blood, Vol. 82, No. 7 (October 1), 1993: pp. 1989–1993, J. H. Griffin et al). Here we demonstrate that the phenotype of APC-resistance is associated with heterozygosity or homozygosity for a single point mutation in the factor V gene (1691, G–A) which predicts the synthesis of a factor V molecule –FV (Q506) or FV Leiden- which is resistance to inactivation by APC. The allelic frequency of the mutation in the Dutch population is about 2% and is at least ten-fold higher than that of all known genetic risk factors for thrombosis (protein C- (Ref. 17), protein S- (Ref. 30), antithrombin III (Ref. 31) deficiency) together (Ref. 32).

Our previous finding that 5% of apparently healthy individuals have a poor anticoagulant response to APC and that this APC-resistance is associated with a seven-fold increase in the risk for deep vein thrombosis (Lancet, Dec. 18, 1993, Vol. 342, pp. 1503–1506, T. Koster et al), prompted us to investigate the molecular basis of this phenotype.

The responsiveness of plasma to APC is measured as the ratio of two Activated Partial Thromboplastin Times (APTT), one measured in the presence of APC and one int its (Lancet, Dec. 18, 1993, Vol. 342, pp. 1503–1506 T. Koster et al; Blood, Vol. 82, No. 7 (October 1), 1993: pp. 1989–1993, J. H. Griffin et al and Ref. 2). For reasons of standarisation this ratio (APC-Sensitivity Ratio or APC-SR) is normalized to the ratio obtained with a reference plasma (n-APC-SR). Resistance to APC is defined by a n-APC-SR<0.84 (1.96 SD below the mean n-APC-SR in 100 healthy controls, after the removal of outliers).

Analysis of the parentships of 14 unrelated APC-resistant patients led to the concept of a familial form of APC-resistance (or APC-cofactor II deficiency (Ref. 2)) where homozygotes and heterozygotes can be identified on the basis of the n-APC-SR (see legend of FIG. 1). Further support for this concept was obtained from mixing experiments (FIG. 1); addition of one volume of normal plasma to one volume of the plasma of a patient classified as homozygous APC-cofactor II deficient (n-APC-R 0.38) results in a n-APC-SR of 0.57. This is identical to the ratio found in plasma of patients classified as heterozygotes for the deficiency (mean n-APC-SR 0.58). Mixing the plasma of four unrelated patients, classified as homozygous APC-cofactor II deficient (mean n-APC-SR 0.40) did not reveal any correction of the ratio, indicating that in all four patients the same plasma protein was missing or defective (see also Ref. 2 and Blood, Vol. 82, No. 7 (October 1), 1993: pp. 1989–1993, J. H. Griffin et al).

To investigate the possibility that APC-cofactor II activity is a functional feature of one of the known blood coagulation proteins, APC-cofactor II levels were measured in a series of plasmas deficient of one single protein (FIG. 2). All these plasmas contained normal APC-cofactor II levels (60–155%) except factor V deficient plasma (<5%). Addition of different amounts of isolated human factor V to factor V deficient plasma introduced both factor V coagulant activity and APC-cofactor II activity.

Independent support for the candidature of factor V as APC-cofactor II was obtained from linkage studies in a large family with APC-resistance (FIG. 3).

The human locus for the factor V gene (F5) has been mapped to chromosome 1 (1q21–25) (Ref. 33). There are no reports of convenient (PCR-able) polymorphic F5 markers. However, variations in published factor V cDNA and genomic sequences (Refs. 20–23) and The Journal of Immunology, Vol. 150, 2992–3001, No. 7, Apr. 1, 1993, N. L. L. Shen et al) aided us to identify two new polymorphisms in the factor V gene. Unfortunately, both were not informative in the APC-resistant family. Therefore we tested the segregation of microsatellite markers for several loci in the 1q21–25 region (see FIG. 4) in this family. The table in FIG. 5 shows the pairwise lodscores for linkage between these markers and the phenotype of APC-resistance. Significantly positive results were obtained only for locus D1S61 (Zmax 7.27 at θ=0.00), which is located within 4 cM from the F5 locus.

At this point we believed to have sufficient indications that APC-resistance is associated with a detect in the factor V gene to start the search for the relevant mutation(s). We focussed our investigations on two regions in factor V, that contain the putative APC binding site (residues 1865–1874) (Refs. 35,36) and the putative APC cleavage site (Arg-506) (Ref. 21 and The Journal of Biological Chemistry, Vol. 262, No. 23, August 15, pp. 11233–11238, 1987, Bruce Odegaard and Kenneth Mann), respectively.

As a first approach, ectopic transcripts of the factor V gene, isolated from peripheral blood lymphocytes, were used for first-strand cDNA synthesis and subsequent amplification of the two regions coding for the APC binding and cleavage site. Direct sequencing of the PCR-fragments revealed that two unrelated patients, classified as homozygous deficient of APC-cofactor II, were both homozygous for a 1691, G→A transition (FIG. 6). This mutation predicts the replacement of Arg-506 (CGA) by Gln (CAA) (FV (Q506) or FV Leiden). No other sequence abnormalities were observed in 225 bp surrounding 1691 A and in 275 bp around the region coding for the putative APC binding site (FIG. 7).

If cleavage after Arg-506 is instrumental for the inactivation of human factor Va by APC, one would predict that introduction of a Gln in position 506 will prevent the inhibitory cleavage. During the coagulation process plasma factor V is initially activated by factor Xa (formation of 105/220 kDa heterodimer (ref. 37)) and next further processed by thrombin (formation of 105/74 kDa heterodimer (Ref. 38)) (Ref. 39). Interestingly, we found that the replacement of Arg-506 by Gln only prevents the inactivation of the Xa-activated form of factor V by APC (FIG. 8) but not that of the thrombin-activated form (data not shown).

The observation that two unrelated APC-resistant patients were homozygous for the same mutation, suggested that this alteration is present in the majority of APC-resistant patients. To investigate this possibility a test was designed for the screening of genomic DNA for the presence of the 1691 G→A transition. Because the mutation is located in exon 10, 11 nt 51 from the start of intron 10 and only the first 8 nucleotides of intron 10 have been published (Ref. 23), more intron 10 sequence was generated by hemi-nested reverse PCR (Ref. 40) (see also sequence 14). From this information primers were designed for the amplification of two overlapping genomic fragments that could be used for genotyping.

Digestion of the 267 bp fragment with Mnl I was used to demonstrate the presence of a normal (1691 G) or mutated allele, while hybridisation of the 222 bp fragment with oligonucleotides specific for the normal or mutated allele was used for the positive identification of 1691 A. Using this approach we first studied all the members of this pedigree from FIG. 3. Complete cosegregation of heterozygosity for the 1691 G→A transition with APC resistance (n-APC-SR<0.84) was demonstrated as shown in FIG. 10 for a part of the pedigree. In addition, 4 patients (II.6, II.8, II.14, III.22) for whom no n-APC-SR was available because they were treated with oral anticoagulants, were found to be heterozygous.

In a previous study of 301 consecutive patients with a first objectively confirmed episode of deep vein thrombosis and 301 age and sex matched population controls. 64 APC-resistant thrombosis patients had been identified (Lancet, Dec. 18, 1993, Vol. 342, pp. 1503–1506, T. Koster et al). These 64 patients and their 64 controls were screened for the presence of the G→A transition. From the 128 individuals 70 had a n-APC-SR<0.84 (64 patients and 6 controls). Fifty six of these carried the mutation (53 patients and 3 controls), six of the patients in both alleles (mean n-APC-SR 0.43; range 0.41–0.44) and the other 50 in one allele (mean n-APC-SR 0.57; range 0.50–0.67). The remaining 14 APC-resistant individuals did not carry the mutation, and had only a marginally reduced n-APC-SR (mean n-APC-SR 0.78; range 0.70–0.83). All 58 non APC-resistant individuals did not carry the mutation (mean n-APC-SR 0.99; range 0.83–1.19). Further none of 100 consecutive thrombosis patients with a n-APC-SR>0.84 was carrier of the mutation, while -as expected-3 of their 100 matched controls were. These 3 (mean n-APC-SR of 0.57, 0.58 and 0.59) were the only controls with a n-APC-SR<0.84.

Our data demonstrate that 80% of the individuals with a n-APC-SR<0.84 and 100% of those with a n-APC-SR<0.70 are heterozygotes or homozygotes for the 1691, G→A transition and that vice versa all carriers of the mutation have a n-APC-SR <0.7. The relatively high frequency of the mutated allele in the Dutch population (about 2%) combined with our previous finding (Lancet, Dec. 18, 1993, Vol. 342, T. Koster et al) that APC resistance is a common and strong risk factor for deep vein thrombosis, makes this hereditary factor V defect the most common hereditary blood coagulation disorder sofar.

FIGS. 1 and 2.

Measurement of APC-cofactor II levels in plasma

FIG. 1. Calibration curve for the assay of APC-cofactor II activity in plasma.

APC-cofactor II refers to the hypothetical new cofactor of APC (Ref. 2) which is missing or defective in individuals with APC-resistance. n-APC-SRs were measured in dilutions of normal plasma (100% APC-cofactor II) in plasma of a patient homozygous deficient of APC-cofactor II (0% APC-cofactor II). The curve in FIG. 1 is the result of nine different experiments. The classification homozygous or heterozygous deficient of APC-cofactor II is based on the results of parentship analysis for 14 probands with APC-resistance (n-APC-SR<0.84). For 2 probands (n-APC-SR 0.38/0.41) both parents were APC-resistant (mean n-APC-SR 0.55); for 11 probands (mean n-APC-SR 0.57) one of the parents was APC resistant (mean n-APC-sR 0.59) while the other was (mean n-APC-SR 0.96); for one proband (n-APC-SR 0.74) both parents were not affected (n-APC-SR 0.96/ 0.99). We propose that individuals can be classified a homozygotes or heterozygotes for APC-cofactor II deficiency on the basis of their n-APC-SR (homozygotes: mean 0.40; n=2; heterozygotes: mean 0.58, range 0.51–0.67, n=26).

FIG. 2. APC-cofactor II activity levels in plasmas deficient (<5%) of a single coagulation factor.

Plasmas were either from patients with a congenital deficiency (a,g, f,m,g,r,s,t) or prepared by immunodepletion (b,c,d,e,j,h,i, k,l,p). Plasmas were deficient of factor II (a), factor VII (b), factor IX (c), factor X (d), factor XI (e), factor XII (j), factor XIII (g), protein C (1), protein S (i), β2-glycoprotein (j), antithrombin (k), factor V (l,m), factor VIII (p,q) or von Willebrand factor (r,s,t). Factor V deficient plasma (m) was supplemented with two different concentrations—54% (n) and 90% (o)—of purified human factor V (Serbio, Gennevilliers, France), dialyzed against 20 mM sodium citrate, 150 mM NaCl, 4 mM $CaCl_2$ and tested for APC-cofactor II activity.

Methods:

The APC-SR was calculated from the results of two APTT measurements, one in the presence of APC and one in its absence, exactly as previously described. (Lancet, Dec. 18, 1993, Vol. 342, T. Koster et al) The n-APC-SR was calculated by dividing the APC-SR for the test sample by the APC-SR for pooled normal plasma. APC-cofactor II activity was measured by reading the n-APC-SR for two different dilutions (1:1, 3:4) of the test plasma in APC-cofactor II deficient plasma on a calibration curve as shown in FIG. 1.

FIGS. 3–5. Linkage analysis in a family with APC-resistance

FIG. 3. Pedigree of a family with APC-resistance (or APC-cofactor II deficiency).

●■, individuals with n-APC-SR<0.94 (mean0.65; range 0.59–0.71, n=13);

0, □, individual with n-APC-SR>0.84 (mean 1.03; range 0.87–1.29;

n=20); ◉, ▨ patients treated with oral anticoagulants (measurement of n-APC-SR in these patients is not meaningful) ⊙, ⊡, individuals that were not treated.

FIG. 4. Integrated genetic linkage map of the q21–25 region of chromosome 1.

The relative positions of the loci AP0A2, D1S104, D1S61, AT3, LAMB and F13B were derived from the NIH/CEPH Collaborative Mapping Group linkage map (Ref. 41). The genetic distance between adjacent loci is given in cM. The F5 locus was placed on this map within 4 cM of the D1S61 locus by studying the segregation of markers for the F5 and D1S61 loci in 3 CEPH families informative for both markers (in 55 meioses no recombination between these two loci was observed $Z_{max}$ 16.6 at θ=0.00).

FIG. 5. Pairwise lodscores of APC resistance with chromosome 1 markers.

All available individuals of the pedigree in FIG. 3 were analyzed. Oligonucleotide sequences for markers for the loci ApoA2, D1S104, D1S61, LAMB and F13B are available from the Genome Data Bank. The primers were obtained from the Dutch primer base. Three different polymorphic markers for the AT3 locus were not informative in this family. Two point linkage analysis was performed using the MLINK programs from the LINKAGE package version 5.3, which was obtained from Dr J. Ott. Sex averaged lodscores are shown.

Methods

Microsatellite markers for ApoA2, D1S104, D1S61, LAMB and F13B were amplified by PCR. Conditions: 50 mM NaCl, 10 mM Tris-HCl (pH 9.6), 10 mM $MgCl_2$, 0.01% BSA, 200 μM dGTP, dATP and dTTP, 20 μM dCTP, 0.7 μCi $\alpha^{32}p$ dCTP, 0.43 U Taq polymerase (Cetus, Emeryville, Calif., USA), 50 ng of each primer and 30 mg genomic DNA. 27 cycles were run at 94° C. (1'), 55° C. (2'), 72° C. (1') with a final elongation step of 10 min. PCR products were separated on a 6% denaturing polyacrylamide sequence gel, after which gels were dried and exposed to X-ray film.

F5 polymorphisms: A 636 bp fragment from exon 13 of the factor V gene (Ref. 23) was amplified by PCR using the primers number 2 (PR-776, nt 2253–2272 (Ref. 21)) and number 3 (PR-768, nt 2870–2899 (Ref. 21)) of the Sequence Listing. For PCR conditions see legend FIGS. 10+11. Restriction with Hinf I detects a C/T dimorphism at nt 2298 (C: 0.68; T: 0.32) and a rare A/G dimorphism at nt 2411 (A:0.98,; G:0.02). None of these markers was informative in the pedigree of FIG. 3.

FIGS. 6–8. Identification of the factor V gene mutation in a patient homozygous deficient of APC-cofactor II FIG. 6. Autoradiogram showing the nucleotide substitution in a patient classified as homozygous deficient of APC-cofactor II.

Part of the nucleotide sequence of the non-coding strand of a cDNA PCR-fragment (coding for aminoacids 417 through 572 in human factor V (Ref. 21)) is shown for one patient (P) and one non APC-resistant control (C). Arrows indicate the location of the 1691, G→A transition, which predicts the replacement of Arg 506 by Gln.

FIG. 7. Schematic representation of the factor V molecule.

Human factor V is a 330 kDa glycoprotein which contains several types of internal repeats. (Ref. 21) Activation by factor Xa results in the formation of a 105/220 kDa heterodimer ($A_1A_2/B'A_3C_1C_2$) (Ref. 38), while activation by thrombin results in the formation of a 105/74 kDa heterodimer ($A_1A_2/A_3C_1C_2$) (Ref. 37). APC binds to the A3 domain of factor Va (Ref. 35,36) and inbibits bovine factor Va by cleavage in the A2 domain after Arg-505 (The Journal of Biological Chemistry, Vol. 262, No. 23, August 15, pp. 11233–11238, 1987, Bruce Odegard and Kenneth Mann).

The amino acid sequences surround the (putative (Ref. 43) APC cleavage site in human (Arg-506) and bovine (Arg-505) factor Va are shown. In the ACP-resistant patient Arg-506 has been replaced by Gln.

FIG. 8. Resistance of factor Xa-activated factor V(Q506) to inactivation by APC.

Al(OH)$_3$-adsorbed and fibrinogen depleted plasma (2 hr 37° C.; 0.3 U ml$^{-1}$ Arvin) containing either factor V(R506) or factor V(Q506) was treated with factor Xa (2 nM) in the presence of 20 mM $CaCl_2$ and 20 μM PS/PC (25/75). After 8 min, when factor V activation was complete, 1.9 mM APC or buffer were added. At different time intervals 10 μl sample was diluted 1/100 in step buffer (50 mM Tris-HCl, pH 7.9, 180 mM NaCl, 0.5 mg ml$^{-1}$ OVA, 5 mM $CaCl_2$) and directly assayed for factor Va activity using the method described by Pieters et al (Ref. 44) The factor Va activity measured after complete activation of 0.70 U m$^{-1}$ FV(R506) (0.64 μM thrombin min$^{-1}$) or 0.49 U ml$^{-1}$ FV(Q506) (0.20 μM thrombin min$^{-1}$) is arbitrary put at 100%; 0, -APC; ●+APC.

Methods cDNA synthesis: RNA was isolated (Ref. 45) from the lymphocyte fraction of 10 ml citrated blood of consenting patients and nonAPC-resistant controls. 1 μg of RNA was used as template for first strand cDNA synthesis in the presence of mixed random hexamers using the superscript kit (BRL, Bethesda, Md., U.S.A.). Amplification of cDNA fragments. The primers Sequence 4 (PR-764, nt 1421–1440 (Ref. 21)) and Sequence 5 (PR-856, nt 1867–1891 (Ref. 21)) amplify the region coding for residues 417 through 572 which contains the putative APC cleavage site; the primers Sequence 6 (PR-849, nt 5608–5627 (Ref. 21)) and Sequence 7 (PR-848, nt 6040–6063 (Ref. 21) amplify the region coding for amino acid residues 1812 through 1963, which contains the APC binding region. PCR conditions were as described in the legend of FIGS. 9+10. PCR fragments were purified on ultra low gelling temperature agarose and directly sequenced as described before (Ref. 42) using the same primers as in the PCR reaction. One additional primer was synthesized to aid in sequencing of the APC-binding region:

Sequence 8(PR-847, nt 5905–5927 (Ref. 21)).

FIGS. 9+10. Association of APC-resistance with the presence of a 1691 A allele of factor V FIG. 9. Cosegregation of 1691 A with APC resistance.

The upper part gives the position of the individuals in the pedigree (FIG. 3) and the n-APC-SR, if available (II6 is on oral anticoagulant treatment). The middle part shows the result of the Mnl I digestion of the 267 bp PCR fragment. The lower part shows the results of the dot blot hybridisation of the 222 bp fragment with the biotinylated oligonucleotide specific for the 1691A allele (PR 1005).

FIG. 10. Dot blot hybridisation of the 222 bp PCR fragments of 64 thombosis patients with a n-APC-SR<0.84 and their 64 matched controls with the biotinylated oligonucleotide specific for the 1691 A allele (PR 1005).

All patients (P) and controls (C) gave their informed consent. Slashes denote positions of failed PCR reactions in this experiment.

Methods

Amplification of genomic fragments containing 1691 G/A. For Mnl-I digestion a 267 bp fragment was amplified using as 5' primer Sequence 9(PR-6967;nt 1581–1602 (Ref. 21)) and as 3' primer primers Sequence 10(PR-990; nt 127 to −146 in intron 10). For dot blot hybridisation a 222 bp fragment was amplified using as 5' primer Sequence 11 (PR-6966, nt 1626–1647 (Ref. 21)) and as 3' primer PR-990 (Sequence 10). Conditions: 125 $\mu$l of a mixture containing 54 mM Tris-HCl (pH 8.8). 5.4 mM $MgCl_2$, 5.4 $\mu$M EDTA, 13.3 mM $(NH_4)_2SO_4$, 8% DMSO, 8 mM β-mercaptoethanol, 0.4 mg $ml^{-1}$ BSA, 0.8 mM of each nucleoside triphosphate, 400 ng of each primer, 200–500 ng DNA and 2U Taq polymerase (Cetus, Emeryville, Calif. USA), was subjected to 36 cycles of 91° C. (40"), 55° C. (40") and 71° C., (2'). The 267 bp fragment (7–10 $\mu$l) was digested with 0.4 U Mnl I (Biolabs, Cambridge, Mass., USA): the 1691 G fragment will give fragments of 67, 37 and 163 bp, while the 1691 A fragment will give fragments of 67 and 200 bp. The 222 bp fragment (about 100 ng) was used for dot blot hybridisation with biotynlated sequence specific oligonucleotide Sequence 12 (PR-1006; nt 1682–1699 (Ref. 21)) for detection of 1691 G and Sequence 13 (PR-1005 for detection of 1691 A. Procedures were exactly as previously described (Ref. 46). After hybridisation stringency washing with PR-1006 was at 53° C., and with PR-1005 at 52° C.

EXAMPLE 2

We investigated the risk of venous thrombosis in individuals heterzygous and homozygous for a mutation in coagulation factor V (factor V Leiden) abnormality. We determined the factor V Leiden genotype in 471 consecutive patients aged under 70 with a first objectively confirmed deep-vein thrombosis and in 474 healthy controls. We found 85 heteroqygous and 7 homozygous individuals among the cases with thrombosis, and 14 heterozygous individuals among the control subjects.

Whereas the relative risk was increased seven-fold for heterozygous individuals, it was increased 80-fold for homozygous individuals. These experienced their thrombosis at a much younger age (32 versus 44 years). The homozygous individuals were predominantly women, with mostly blood group A.

Because of the increased risk of thrombosis with age, the absolute risk difference is most pronounced in older patients, both for heterozygous and homozygous individuals. For the homozygous individuals, the absolute risk becomes several percent per year. This implies that most individuals homozygous for factor V Leiden will experience at least one thrombotic even in their lifetime.

Because of the high allele frequency of the mutated factor V gene, homozygous carriers will not be extremely rare as in other types of hereditary thrombophilia. It was unknown to data whether the homozygous state confers a higher risk than the heterozygous state. We have estimated the risk of thrombosis and the clinical features of patients who were homozygous for Factor V Leiden. These were identified in a large case-control study on deep-venous thrombosis (The Leiden Thrombophilia Study: LETS) (Koster T, et al. Venous thrombosis due to poor anticoagulant response to activated protein C: Leiden Thrombophilia Study. Lancet 1993; 342: 1503–1506).

Methods

Study design.

The details of the design of LETS have been described previously (Koster T, et al. Venous thrombosis due to poor anticoagulant responser to activated protein C: Leiden Thrombophilia Study. Lancet 1993; 342: 1503–1506). We included consecutive patients younger than 70 years, who were referred for the out-patient monitoring of anticoagulant treatment to the Anticogulation Clinics of Leiden, Amsterdam and Rotterdam, after a first, objectively confirmed episode of deep-vein thrombosis, in the absence of known malignant disorders. Patients were seen at least six months (range 6–19 months) after the acute thrombotic even. 90% of eligible patients were willing to take part in the study. In addition to 474 thrombosis patients, we included 474 control subjects who had no history of venous thromboembolism, did not suffer from known malignancies, and were of the same sex and approximately (plus/minus 5 years) the same age.

Data collection and laboratory analysis.

All subjects completed a standard questionnaire, which contained questions about the presence of acquired risk situations in the past, confined to a specific period prior to the index date, i.e. date of the thrombotic event. As acquired risk situations we considered surgery, hospitalization without surgery or prolonged immobilization at home ($\geq 2$ weeks), all in the year preceding the index data, and pregnancy at the time of the index date.

Blood was collected from the antecubital vein into Sarstedt Monovette® tubes, containing 0.106 mmol/L trisodium citrate. High-molecular-weight DNA was isolated from leucocytes and stored at 4° C. The presence of the mutant factor V-Leiden gene (1691, G→A transition) was determined as described. By this method we established for each patient whether he was homozygous normal (GG), heterozygous (AG) for the factor V Leiden mutation, or a homozygous carrier (AA) of this abnormality. The technicians were at all times blinded to the status of the sample, i.e. whether it was from a patient or a control subject. Cells for DNA analysis were available for 471 patients and 474 controls.

Analysis and statistics.

The frequency of heterozygous and homozygous carriers of the factor V Leiden mutation in cases and controls was compared by simple cross-tabulation. Since in the analysis of the risk associated with the heterozygous state sex and age did not appear to be confounding variables, as they were not expected to be for autosomal genetic abnormalities, relative risk estimates for the heterozygous state were obtained by calculation of unmatched exposure odds ratios. A 95% confidence interval was constructed according to Woolf (Woolf B. On estimating the relation between blood group and disease. Ann Hum Genet 1955; 19:251–253).

The risk associated with the homozygous state could not be estimated in this standard fashion, since no homozygous individuals were found among the controls. Therefore, under the assumption of Hardy-Weinberg equilibrium (in the controls) the expected number of homozygous individuals in a control population was calculated, and the odds ratio was subsequently estimated in the standard fashion. The variance of the (log) odds ratio for the homozygous state was estimated by a modification of the method of Woolf. When each cell of the two-by-two table with cell contents a, b, c and d is considered to be the realisation of a Poisson distribution, and variance of the log(OR) is 1/a+1/b+1/c+1/d (Woolf B. On estimating the relation between blood group and disease. Ann Hum Genet 1955; 19:251–253). When the number of individuals with GG and AA genotypes are counted in the cases and calculated from Hardy-Weinberg equilibrium for the controls, which requires a quadratic transformation, the variance of the log(OR) becomes 1/AA (cases)+1/GG (cases)+4/A (controls)+4/A (control)+4/G (control), in which AA and GG are the number of genotypes (individuals), and A and G the number of alleles.

The absolute risk for thrombosis for the various genotypes and ages was calculated by first partitioning the number of person-years in the origin population (as derived from information from the municipal authorities) under the assumption of Hardy-Weinberg equlibrium. Dividing the cases in each subgroup (genotype, age) by these person-years, leads to estimates of the absolute risks. Subsequently, these crude incidence data were modelled after logarithmic transformation in a weighted least square regression model, with three age classes (0–29: 25 yrs: 30–49: 40 yrs: 50–69: 60 yrs), indicator variable for the heterozygous (0,1) and the homozygous state (0,1), weighted for the number of cases in each stratum. This method in which stratum-specific incidence rates are first estimated and then smoothed ('smooth-last [Greenland S. Multivariate estimation of exposure-specific incidence from case-control studies. J. Chron. Dis. 1981; 34: 445–453]) by weighted least square regression has been described by Grizzle et al (Grizzle J E, Starmer C F, Koch G G, Analysis of categorical data by linear models. Biometrics 1969; 25: 489–504). Since for a Poisson distribution the various of the number of cases equals the number of cases, this is almost identical to fitting a Poisson regression model. This model will lead to more stable estimates, especially for the homozygous state, under the assumption that the incidence rate ratio for the homozygous state (and the heterozygous state) is constant over the age strata for the log (incidence rate). This model can be written as:

Log(I)=$\alpha$+$\beta_1$*age+$\beta_2$*AG(0,1)+$\beta_3$*AA(0,1), which can subsequently be used to calculate estimates for the absolute risk and for the relative risk (as the antilogarithm of the coefficients).

Results

Among 471 patients, we found 85% (18%) who were heterozygous and seven (1,5%) who were homozygous for the defect, whereas the other 379 (80%) did not carry the Factor V Leiden mutation. Among the 474 controls, 14 (2.9%) were heterozygous and all other 460 were normal: there were not homozygous individuals among the controls.

The homozygous individuals experienced thrombosis at a markedly younger age than the other patients: the median age at thrombosis was 32 years, as compared to 44 years in the heterozygous, and 46 years in the patients without the mutation (table 2).

The clinical course of the deep vein thrombosis in the homozygous patients was unremarkable. All suffered from deep venous thrombosis of the leg. Four were briefly hospitalised for heparinisation, three were treated as outpatients with cumarin derivatives only. None of the seven patients had a history of overt arterial disease (myocardial infarction, stroke or peripheral arterial disease) (table 3).

Six (86%) of the seven homozygous patients were women, as compared to 46 (54%) of the heterozygous and 217 (57%) of the individuals without the mutation. Also, six of these seven patients had blood group A, as compared to 249 (54%) of the other 464 cases. Of the five homozygous women of 45 years and younger, three used oral contraceptives at the time of the thrombotic event, which was similar to current use in all cases. Since non-O blood group and use of oral contraceptives are in themselves risk factors for venous thrombosis, these figures indicate an interaction between these risk factors and homozygous factor V Leiden which is of a multiplicative nature.

In two (29%) of the seven homozygous patients there had been a predisposing factor for thrombosis in the year preceding the event (one had hip surgery 45 days prior to the thrombosis, and one had been admitted to hospital overnight after giving birth 60 days prior to the thrombotic event). Among the 85 heterozygous individuals an acquired risk factor had been present in 25 (29%) patients, and among the normal patients in 131 (35%) of 379).

Previous risk situations (operations, pregnancies, hospital admissions) without thrombotic consequences were less frequent in the patients homozygous for factor V Leiden than in the other patients. Still, five of the seven homozygous patients had encountered risk situations in the past without a subsequent thrombosis (two had surgery, four had given birth to five children).

The seven patients were followed on average for two years without long-term oral anticoagulation after the first thrombotic event. One patient had a recurrent thrombosis (1/13.4 yr: 7.4 percent per year). Of the 14 parents, three had a history of venous thrombosis, which is approximately five times higher than expected.

Under Hardy-Weinberg equilibrium, the relative frequency of normals:heterozygotes:homozyzygotes is $p^2$:2 pg:$q^2$, in which p is the allele frequency of the normal gene and q of the abnormal gene. Since $p^2$:2 pg was 460/474:14/ 474, it follows that the allele frequency of factor V Leiden (q) is 0.0.15. The allele frequencies of p=0.985 and q=0.015 conform to a distribution among 474 unselected individuals of 459.9 (GG), 14.0 (AG) and 0.107 (AA).

The expected number of homozygous individuals ($q^2$) of 0.107 among 474 controls leads to an odds ration for the homozygous state of (7/379)/(0.107/460)=79. So, the risk of thrombosis for homozygous individuals is almost eighty times increased compared to normal individuals (CI95%: 22 to 289).

Table 4 shows the odds ratio for the three age groups, when the allele frequency of 0.015 is used to calculate the expected number of homozygous controls in each age group. It is evident that the high relative risk of thrombosis in homozygous individuals diminishes with advancing age. This is in contrast to the relative risk for heterozygous individuals, which is more or less constant over age.

Subsequently, we calculated absolute risks (incidence rates) for the different age groups and genotypes, by using data on the age-distribution in the origin population, and under the assumption of Hardy-Weinberg equilibrium. As is shown in table 4, the incidence increases from only 0.55 per 10,000 per year in the youngest age group with GG genotype, to 16.3 per 10,000/year for heterozygous individuals in the older age groups. It is also clear from the figures in table 4, that at all age groups the risk for homozygous individuals is much higher than for heterozygous individuals (78 to 176 per 10,000 per year). However, since these figures are based on only seven individuals divided over three age groups, the estimates are unstable, and show an unexpected lower incidence in the oldest age group. The regression model we used smooths these estimate, since it assumes a constant relative risk over the age groups. As FIG. 12 shows, this model fits excellently for the normal and heterozygous individuals (coefficients:constant:−10.06, age: 0.0293, AG:1.96, AA:4.52). The smoothed incidence estimates for homozygous individuals now increase from 82 per 10,000 person-years in those aged under 30, to 227 per 10,000 patients-years for those aged 50–69 (FIG. 13). These estimates imply that the most homozygous patients will experience at least one thrombotic event in their lifetime.

Discussion

Resistance to APC is a common abnormality with an allele frequency for the mutant factor V gene of about 1.5 percent. This implies that three percent of the population is heterozygous, and homozygous individuals can be expected with a prevalence of about two per 10,000 births.

In this study we show that homozygous individuals have a high risk of thrombosis, which is also considerably higher than the risk of heterozygous individuals. This conclusion finds support in the young age at which the homozygous individuals experienced their first thrombotic event.

It is clear that the risk of thrombosis in homozygous factor V Leiden is nowhere near the risk of thrombosis in homozygous protein C or protein S deficiency; these abnormalities lead to neonatal purpura fulminans (Branson H E, et al. Inherited protein C deficiency and coumarin-responsive chronic relapsing purpura fulminans in a newborn infant. Lancet 1983; ii: 1165; Mahasandana C, et al. Neonatal purpura fulminans associated with homozygous protein S deficiency. Lancet 1990; 335: 61–62). All of the individuals with homozygous factor V Leiden lived until adulthood before the first thrombotic event, and one even until late middle age. Most of the homozygous individuals had experienced risk situations in the past without thrombosis, for most of which (pregnancy, puerperium) no anticoagulant prophylaxis will have been prescribed. This shows that APC-resistance should be seen as a quantitative defect (decreased inactivation rate of factor Va) rather than a qualitative defect (no protein C activity) as in homozygous protein C deficiency.

A remarkable finding in this study was the predominance of women among the homozygous patients. Since among these women the use of oral contraceptives was as prevalent as among the other cases, it is likely that this use played a role by a synergistic effect with APC-resistance. Since both pill use and APC-resistance are common, further studies should investigate this association, especially for the heterozygous carriers (3 percent of all women).

The relative risk for heterozygous individuals appears constant for the different age groups. This observation has to be seen in the light of a background incidence that increases with age. This implies, as we showed in FIGS. 12 and 13 that the absolute risk of thrombosis, or the absolute risk added by APC-resistance, becomes substantial for older heterozygous individuals.

It may be noted that our overall estimate for the incidence rate, at about 2 per 10,000 per year, is lower than the usual estimates of about 0.5 to 1 per 1000 person-year (Branson H E, et al. Inherited protein C deficiency and coumarin-responsive chronic relapsing purpura fulminans in a newborn infant. Lancet 1983; ii: 1165; Koster T, More objective diagnoses of venous thromboembolism Neth. J. Med. 1991; 38: 246–248). This is most easily explained by the age limits in our study (<70 years), by the restriction to confirmed thromboses, by the exclusion of patients with malignancies and by the restriction to first thrombotic events.

The homozygous patients had a risk of thrombosis that was eighty times increased, which leads to an overall incidence of about 1 percent per year. The observed decrease of the rate in the older age groups, may be explained by a scarcity of individuals of that age in the population who had not already experienced a first thrombotic event. It may also have been the result of the small number of homozygous patients (i.e. only one in the oldest age group). In both instances, the incidence figures that were recalculated from the weighted regression model seem the best estimate of the risk, which becomes over two percent per year in patients aged 50 and older.

We conclude that APC-resistance caused by homozygous factor V Leiden leads to a high risk of deep venous thrombosis. This thrombosis appears not to occur before aldulthood, and even does not invariably become apparent in risk situations such as pregnancy and puerperium. Therefore, although we are convinced that these patients should receive short-term prophylaxis with anticoagulants in risk situations. Life-long prophylaxis in individuals homozygous for factor V Leiden may however not necessarily be required.

TABLE 2

General characteristics of 471 thrombosis patients by factor V genotype

|  | GG | AG | AA |
|---|---|---|---|
| n | 379 | 85 | 7 |
| Age |  |  |  |
| median (yr) | 46 | 44 | 31 |
| range (yr–yr) | 15–69 | 17–69 | 22–55 |
| Sex |  |  |  |
| men (%) | 162 (43) | 39 (46) | 1 (14) |
| women (%) | 217 (57) | 46 (54) | 6 (86) |

GG: homozygous normal factor V
AG: heterozygous for factor V Leiden
AA: homozygous for factor V Leiden

TABLE 3

Detailed characteristics of seven homozygous patients.

| Patients id | Sex | Age | APC-SR | blood group | OCC[1] | Pre-disposing 1 yr < VT | factors[2] intervals[3] | DVT parent[4] | arterial disease[5] |
|---|---|---|---|---|---|---|---|---|---|
| 90  | F | 55 | 1.13 | A | —  | N    | —  | 0 | N |
| 124 | F | 24 | 1.14 | A | N  | Y[6] | 60 | 0 | N |
| 266 | F | 30 | 1.20 | A | Y  | N    | —  | 0 | N |
| 173 | F | 22 | 1.14 | O | Y  | N    | —  | 0 | N |
| 583 | F | 44 | 1.23 | A | N  | Y[7] | 45 | 1 | N |
| 589 | F | 42 | 1.21 | A | Y  | N    | —  | 1 | N |
| 944 | M | 31 | 1.19 | A | —  | N    | —  | 1 | N |

[1] use of oral contraceptives in the month preceding the thrombosis
[2] surgery, hospital admission, immobilisation in the year preceding the thrombosis, childbirth one month prior to the thrombosis, pregnancy at the time of the thrombosis
[3] number of days between risk situation and thrombosis
[4] number of parents with a history of venous thrombosis
[5] previous myocardial infarction, stroke or peripheral arterial disease
[6] overnight hospital stay after giving birth
[7] hip surgery

TABLE 4

Odds ratios and absolute risk of first thrombosis by age

| | Cases | controls | | | | Person- | Incidence rates per $10^{-4}$ year[1] | | |
|---|---|---|---|---|---|---|---|---|---|
| Age | GG/AG/AA | GG/AG | $E_{AA}$ | $OR_{AA}$ (CI95) | $OR_{AG}$ (CI95) | year | AG | AG | AA |
| 0–29  | 61/17/2  | 70/3  | .0164 | 140 (1.8=23) | 6.5 (1.8=23) | 1,134,681 | 0.6 | 5.1  | 78.4  |
| 30–49 | 176/35/4 | 217/6 | .0502 | 98 (15=650)  | 7.2 (3.0=17) | 1,006,733 | 1.8 | 11.8 | 176.2 |
| 50+   | 142/33/1 | 173/5 | .0400 | 30 (2.2=429) | 8.0 (3.1=21) |   682,939 | 2.1 | 16.4 | 110.0 |

$E_{AA}$ expected number of homozygous individuals among controls based on overall Hardy-Weinberg equilibrium ($q^2$ $n_{controls\ in\ age-stratum}$, q = .015)
$OR_{AA}$ odds ratio for homozygous individuals (versus homozygous normals)
$OR_{AG}$ odds ratio for heterozygous individuals (versus homozygous normals)
CI95 95%-confidence interval
[1] crude incidence rates, based on the number of observed cases over the number of patient-years, partitioned according to Hardy-Weinberg equilibrium FIGS. 12 and 13.

Crude (FIG. 12) and smoothed (FIG. 13) incidence rates estimates for factor V Leiden genotypes by age.

The lowest line shows the estimates for the GG genotype, and the upper line for the AG genotype (in the figure). FIG. 13 also shows the estimates for the AA genotype (homozygous factor V Leiden). Crude incidence estimates are indicated by +, whereas the smoothed rates are indicated by □. The smoothed incidence rates per 10,000 person-years were, for GG: 0.9 (0–20 yr), 1.4 (30–49 yr) and 2.5 (50–69 yr); for AG: 6.3 (0–29 yr), 9.8 (30–49 yr), 17.6 (50–69 yr); for AA: 81.5 (0–29 yr), 126.5 (30–49 yr) and 227.3 (50–69 yr).

EXAMPLE 3

Plasmids and in vitro RNAs

RNA isolated from PBMCs of a healthy person (homozygous wild-type) and of two patients, ID90 and ID137 (homozygous mutant, both) was obtained from the Hemostatis and Thrombosis Research Centre, Leiden, the Netherlands. Fragments of 297 nt encompassing the mutation at position amino acid 506 were cloned in the vector pG30 using the restriction enzymes EcoRI and Csp451. The resulting plasmids were named pG30/FVwt and pG30/FVmut for wild-type and mutant clones respectively.

Cloning of the correct sequence was confirmed by sequence analysis and subsequently the plasmids were purified by CsCl gradient for in vitro RNA synthesis. Using plasmid pG30/FVwt as a source a system control plasmid (pG30/FV E2) was constructed by deletion of the probe sequence (21 nt) and insertion of the E2 sequence (144 nt). The 3 plasmids described above were used for in vitro RNA transcription using T7 RNA polymerase in the standard protocol. The plasmids were linearized with BamHI which, after transcription with T7 RNAP, would result in RNAs consisting of 297 nt and 420 nt of respectively the wt, mut and system control clones followed by 700 nt of vector sequence, so that the overall length of the in vitro RNA would be approximately 1 kb. After in vitro transcription the RNA was treated with DNase I, purified using the Tip 100 column (Qiagen) protocol and quantitated spectophotometrically. Appropriate serial dilutions were made in water and the in vitro RNAs were stored at −70° C.

Primers and probes.

The sequences of the NASBA amplification primers and detection probes for ELGA and ECL detection are given in table 5.

TABLE 5 primers and probes for Factor V NASBA

| Name | Sequence | Length (nt) | Remarks |
|---|---|---|---|
| P1 | 5'<u>ATT TCT AAT ACG ACT CAC TAT AGG GAA</u> GGT ACC AGC TTT TGT TCT CA 3' (SEQ. ID. NO. 15) | 47 | |
| P2 | 5'AGT GCT TAA CAA GAC CAT ACT A 3' (SEQ. ID. NO. 16) | 22 | |
| Generic ELGA-probe | 5'TGA CGT GGA CAT CAT GAG AGA 3' (SEQ. ID. NO. 17) | 21 | HRP-labelled |
| Generic ECL-probe | 5'CAG CAG GCT GTG TTT GCT GTG 3' (SEQ. ID. NO. 18) | 21 | ECL-labelled |
| WT-probe | 5'CTG GAC AGG CGA GGA ATA CAG 3' (SEQ. ID. No. 19) | 21 | HRP-labelled or biotin-labelled |
| Mut-probe | 5'CTG GAC AGG CAA GGA ATA CAG 3' (SEQ. ID. NO. 20) | 21 | HRP-labelled or biotin-labelled |
| SC-probe | 5'GAC ACC AAG GAA GCT TTA GAC3' (SEQ. ID. NO. 21) | 21 | biotin-labelled | a. The underlined part in the P1 sequence is the T7 RNAP promoter sequence.

The P1 is located in exon 10 of the Factor V coding sequence, while the P2 sequence is located in exon 11. As a result this primer set can only amplify mRNA sequences from which the intron 10 sequence is removed by splicing. Due to better performance in either ELGA or ECL there are two generic probes. However, it should be possible to choose one generic probe for both ELGA and ECL. The amplification primers were purified on 20% acryl amide, 7M urea slab gels. After elution and EtOH precipitation the primers were dissolved in 500 µl H$_2$O and the concentration determined by spectophotometry (OD260).

Biotin oligos were made on the synthesizer and used after EtOH precipitation and dissolving in H$_2$O. Coupling the HRP label to NH$_2$-oligos was done according to the standard protocol and the probe was used without further purification (generic ELGA probe) or purified on a slab gel (wild-type and mutant specific ELGA probes). The ECL oligos were synthesized and used without further purification.

Nucleic acid isolation.

All nucleic acid isolations were performed using the method described by Boom et al. (1990, J. Clin. Microbiol 28: 495–503). Nucleic acid was extracted from 100 µl whole blood (see clinical samples) and elution was in 100 µl H$_2$O, typically 5 µl of eluate was used as input for NASBA amplification. The remainder of the eluate was stored at −70° C.

NASBA amplifications.

NASBA amplifications were performed as follows. To 5 µl of RNA 18 µl of a premix solution was added that consisted of: 10 µl 2.5×NRG buffer (final concentration in 1×buffer: 40 mM tris, pH=8.5, 70 mM KCl, 1 mM each dNTP, 2 mM ATP/CTP/UTP, 1.5 mM GTP, 0.5 mM ITP, 12 mM MgCl$_2$), 6.25 µl 4×primer mix (final concentration in 1×buffer: 15% v/v DMSO, 0.2 µM P1 and 0.2 µM P2) and 1.75 µl H$_2$O. The sample was incubated at 65° C. for 5 minutes and subsequently incubated at 41° C. for 5 minutes. Leaving the tubes as much as possible at 41° C. 2 µl enzyme mix (8 units AMV-RT, 40 units T7 RNAP, 0.1 unit *E. coli* RNase H, 2.6 µg BSA, 1.5 M sorbitol) was added, followed by gentle mixing (i.e. tapping) and incubation at 41° C. for 90 minutes.

ELGA detection.

For ELGA detection 3 different probe solutions were used containing a generic probe, wild-type probe and mutant probe respectively. In order to increase the specificity of the wild-type and mutant HRP labelled probes, these labelled probes were mixed with their counterpart non-labelled probe (see table 6).

TABLE 6

Ratios of labelled and non-labelled probes to increase the specificity of hybridization for ELGA detection

| Amplificate to detect | HRP-labelled probe (molec/hyb) | non-labelled probe (molec/hyb) |
|---|---|---|
| Generic[a] | ELGA Generic (2 × 10$^{10}$) | — |
| Wild-type | Wild-type (2 × 10$^{11}$)[b] | Mutant (5 × 10$^{13}$) |
| Mutant | Mutant (2 × 10$^{11}$)[b] | Wild-type (2 × 10$^{13}$) |

[a]This includes: wild-type, mutant and system control amplificates
[b]Due to the purification process (slab gel) the specific activity of the wild-type and mutant HRP probes is lower than normal.

After amplification 1 µl of amplificate was added to 4 µl of appropriate probe mix (final concentration in 5 µl: 1×SSC, BFB, XCFF, 5% v/v glycerol and the appropriate probes, see table 2), mixed and incubated for 15 minutes at 45° C. Subsequently 2.5 µl of the sample was analyzed on an acrylamide gel (5% acryl/bisacryl, 0.04% dextrane sulphate, NASBA elfo buffer=25 mM tris, 25 mM boric acid, 500 µM EDTA, pH=8.3) run at 150 V in 0.5×NASBA elfo buffer. After electrophoresis the gel was stained using the standard TMB/UP substrate solutions (mixed at 1:1 ratio) for approximately 6 minutes. Usually the gels were fixed in 50% methanol (0/N) and air dried between 2 sheets of transparent foil.

ECL detection.

For ECL also 3 different probe solutions were used for detection of amplificate (see table 7).

TABLE 7

Ratios of labelled and non-labelled probes to increase the specificity of hybridization for ECL detection.

| Amplificate to detect | ECL-labelled probe (molec/hyb) | Biotin capture probe (molec/hyb) | Non-labelled probe (molec/hyb) |
|---|---|---|---|
| Wild-type | ECL generic ($2 \times 10^{12}$) | Wild-type ($2 \times 10^{12}$)[a] | Mutant ($2 \times 10^{13}$) |
| Mutant | ECL generic ($2 \times 10^{12}$) | Mutant ($2 \times 10^{12}$)[a] | Wild-type ($8 \times 10^{12}$) |
| System control | ECL generic ($2 \times 10^{12}$) | SC ($2 \times 10^{12}$) | — |

[a]Streptavidin coated beads for 100 hybridisation (200 µl Dynal beads) reactions were loaded with $2 \times 10^{34}$ molecules biotin capture probes.

To set up the hybridisation reaction 10 µl ECL mix (0.1% w/v BSA, 12.5×SSC, $2 \times 10^{12}$ molecules ECL generic probe), 10 µl bead mix (0.1 w/v BSA, 1×PBS, 2 µl appropriate bead solution and the appropriate non-labelled probe) and 5 µl 21 fold diluted (in water) amplificate were mixed and incubated for 30 minutes at 45° C. under constant shaking in a stove. Subsequently 300 µl ECL assay buffer was added and the tubes placed in the ECL instrument for reading of ECL signals.

Results

Sensitivity.

The primers used for NASBA amplification of the Factor V mRNA generate an amplificate of 182 nt long for the wild-type and mutant sequence. When the primers are used for amplification of the system control (SC) in vitro RNA the result is an amplimer of 305 nt in length. The sensitivity of the amplification was investigated using serial dilutions of in vitro generated wild-type, mutant and SC RNA (Table 8).

TABLE 8

Sensitivity of the Factor V mRNA NASBA using ELGA detection with the generic ELGA probe

| Input RNA | Amount (molecules) | ELGA results |
|---|---|---|
| Wild-type | $10^4$ | + |
|  | $10^3$ | + |
|  | $10^2$ | + |
|  | $10^1$ | − |
|  | $10^0$ | − |
| Mutant | $10^4$ | + |
|  | $10^3$ | + |
|  | $10^2$ | + |
|  | $10^1$ | + |
|  | $10^0$ | − |
| SC | $10^4$ | + |
|  | $10^3$ | + |
|  | $10^2$ | + |
|  | $10^1$ | ± |
|  | $10^0$ | − |

For all 3 input RNAs the analytical sensitivity is at least 100 molecules. The reactions with an input of 10 molecules are occasionally positive, indicating that the sensitivity is actually between 10 and 100 molecules.

EXAMPLE 4

The methods used are as described for example 3.

In order to determine the amount of SC RNA that should be spiked in the nucleic acid isolation without competing with the wild-type of mutant RNA when present, several amounts of SC RNA were analyzed. These SC RNA amounts were isolated without addition of sample, with the addition of 100 µl whole blood and as a control a dilution series of SC RNA was directly amplified. The results of ELGA analysis after amplification are depicted in table 5. Apparently there is some loss of nucleic acid during nucleic acid isolation (compare lanes 3 with and without isolation, A and C, respectively).

From the A series (table 9) it can be concluded that the minimum amount of SC RNA that should be spiked in the lysisbuffer is $1 \times 10^5$ molecules. This amount of SC RNA is not inhibitory for the amplification of wild-type or mutant RNA isolated from 100 µl whole blood. In fact, even when 10 times more SC RNA is used, this is not inhibitory for wild-type or mutant RNA isolated from 100 µl whole blood (table 5, B series). In all further experiments, when appropriate, $10^5$ molecules of SC RNA were spiked in the lysisbuffer before nucleic acid isolation.

TABLE 9

ELGA results of amplification of different amount of System control RNA spiked before nucleic acid isolation

| Input | Set-up | SC signal | Wt/Mut signal |
|---|---|---|---|
| 1 | A | + | − |
| 2 | A | + | − |
| 3 | A | − | − |
| 4 | A | − | − |
| 1 | B | − | + |
| 2 | B | − | + |
| 3 | B | − | + |
| 4 | B | − | + |
| 1 | C | + | − |
| 2 | C | + | − |
| 3 | C | + | − |
| 4 | C | − | − |

ELGA results of amplification of different amount of CS RNA spiked before nucleic acid isolation
A Nucleic acid isolation without addition of sample
B Nucleic acid isolation with 100 µl whole blood
C control, direct amplification of SC RNA
1 $1 \times 10^6$ molecules SC RNA in lysis buffer (± $5 \times 10^4$ per amplification)
2 $1 \times 10^4$ molecules SC RNA in lysisbuffer (± $5 \times 10^3$ per amplification)
3 $1 \times 10^4$ molecules SC RNA in lysisbuffer (± $5 \times 10^2$ per amplification)
The probe used for hybridization was the generic ELGA probe.

EXAMPLE 5

The methods used are as described in example 3

Due to the nature of the mutation in the Factor V mRNA, a G→A single base mutation, it is expected that the wild-type probe will give considerable background signal on mutant amplificate and vice versa. This will be the case for both ELGA and ECL detection. In order to avoid complicated hybridization protocols the labelled probes are mixed with their non-labelled counterpart to suppress background hybridization on the non-homologous amplificate. In table 10 the results of specific detection of wild-type and mutant amplificates with probe mixtures are depicted, using ELGA detection.

TABLE 10

ELGA detection of wild-type mutant amplificates with specific wild-type (WT) and mutant (Mut) probes labelled with HRP.

| Labelled probe | Non-labelled probe | Excess non-labelled probe | WT-signal | Mut signal |
|---|---|---|---|---|
| WT | Mut | 1 | ++ | ++ |
|  |  | 5 | ++ | ++ |
|  |  | 10 | ++ | + |
|  |  | 100 | ++ | ± |

TABLE 10-continued

ELGA detection of wild-type mutant amplificates with specific wild-type (WT) and mutant (Mut) probes labelled with HRP.

| Labelled probe | Non-labelled probe | Excess non-labelled probe | WT-signal | Mut signal |
|---|---|---|---|---|
| | | 250 | ++ | − |
| | | 500 | + | − |
| Mut | WT | 1 | + | ++ |
| | | 5 | + | ++ |
| | | 10 | ± | ++ |
| | | 100 | − | ++ |
| | | 250 | − | ± |

WT = wild-type HRP-labelled probe; Mut = mutant HRP-labelled probe

It is apparent that in case of the wild-type HRP labelled probe a 250 fold excess of non-labelled mutant probe should be added to reduce the background sufficiently. When the HRP-labelled mutant probe is used, an excess of 100 fold non-labelled wild-type probe is sufficient to reduce the background to an acceptable level. A more or less identical experiment was performed using ECL detection. In the ECL method the non-labelled probe has to compete with the specific biotinylated capture probe on the magnetic bead. The result of the ECL detection using different excess non-labelled probe ratios is depicted in Table 11.

TABLE 11

ECL detection of wild-type and mutant amplificates with specific wild-type (WT) and mutant (Mut) probes.

| Labelled probe | Non-labelled probe | Excess non-labelled probe | WT-signal (x1000) | Mut signal (x1000) |
|---|---|---|---|---|
| WT | Mut | 0 | 620 | 250 |
| | | 1 | 250 | 20 |
| | | 2.5 | 300 | 1 |
| | | 5 | 200 | 1 |
| | | 10 | 100 | 0 |
| Mut | WT | 0 | 300 | 600 |
| | | 1 | 2 | 200 |
| | | 2.5 | 3 | 100 |
| | | 5 | 0 | 80 |
| | | 10 | 0 | 30 |

WT = wild-type HRP-labelled probe; Mut = mutant HRP-labelled probe

For subsequent ECL detection an excess of 10 fold non-labelled mutant probe with biotinylated wild-type probe on beads and an excess of 4 fold non-labelled wild-type probe with biotinylated mutant probe on beads was used. The differences between amount of non-labelled probe that has to be added for ELGA and ECL detection has to do with the hybridization formats. In the ECL format the specific probe is bound to the magnetic bead and therefore will have slower hybridization kinetics compared to probes in solution. As a result a relatively small excess of in solution non-labelled probe has to be added. In the ELGA the competition takes place between 2 probes in solution, which makes it necessary to add a relatively high amount of non-labelled probe.

References

1. Hirsch, J., Hull, R., Raskob, G. E. Epidemiology and pathogenesis of venous thrombosis. *J. Am. Coll. Cardiol.* 1986; 8:104B–113B
2. Dahlbäck, B., Carlsson, M., Svensson, P. J. *Proc. Natl. Acad. Sci.* 1993; 90:1004–8
3. Clouse, L. H., Comp, P. C. *New Engl. J. Med.* 1986; 314:1298–1304
4. Esmon, C. T., Protein-C: biochemistry, physiology, and clinical implications. *Blood* 1993; 62:1155–1158
5. Bakker, H. M., Tans, G., Janssens-Claessen, T., Thomassen, M. C. L. G. D., Hemker, H. C., Griffin, J. H., Rosing, *J. Eur. J. Biochem.* 1992; 208–171–1786
6. Koedam, J. A., Meijers, J. C. M., Sixma, J. J., Bouma, B. N. *J. Clin. Invest.* 1988; 82:1236–1243
7. Svensson, P. J., Dahlbäck, B. *Thromb. Haemostas.* 1993; 69:1252
8. Svensson, P. J., Dahlbäck, B. *Thromb. Haemostas.* 1993; 69:999
9. Dahlbäck, B., Malm J., *Thromb. Haemostas.* 1993; 69:529
10. Walker, F. J., Sexxton, P. W. & Esmon, C. J. Biochim. Biophys. Acta 1979; 571: 333–342
11. Boyer-Neumann, C., Bertina, R. M., Tripodi, A., D'Angelo A., Wolf M., Vigano D'Angelo, S., Mannucci, P. M., Meyer, D., Larrieu, M. J. Comparison of functional assays for protein S; European collaborative study of outpatients with congenital and acquired deficiency. *Thromb. Haemostas.* 1993; 70(6):946–950.
12. Canfield, W., Nesheim, M., Kisiel, W. & Mann, K. G. Circulation. 1978; 58: II-210.
13. Suzuki, Kl, Stenflo, J., Dahlbäck, B & Teodorsson, B. J. Biol. Chem. 1983; 258: 1914–1920.
14. Tracy, P. B., Nesheim, M. E., and Mann, K. G. J. Biol. Chem. 1983; 258: 662–669.
15. Miletich, J., Sherman, L., Broze, G., *N. Engl. J. Med.* 1987; 317–991–996
16. Miletich, J. P., Prescott, S. M., White R., Majerus, P. W., Bovill, E. G., *Cell* 1993; 72:477–480
17. Allaart, C. F., Poort, S. R., Rosendaal, F. R., Reitsma, P. H., Bertina, R. M., Briët, E., *Lancet* 1993; 341:134–138
18. Heijboer, H., Brandjes, D. P. M., Büller, H. R., Sturk, A., ten Cate, J. W., *N. Engl. J. Med.* 1990; 323:1512–1516
19. Potzsch, B., Kawamura, H., Preissner, K. T., Schmidt, M., Seelig, C., Muller-Berghaus, G. *Blood* 1992; 80:267A (Abstr.)
20. Kane, W. H., Davie, E. W. *Proc. Natl. Acad. Sci. USA* 1986; 83:6800
21. Jenny, J. R., Pittman, D. D., Toole, J. J., Kriz, R. W., Aldape, R. A., Hewick, R. M., Kaufman, R. J., Mann, K. G. *Proc. Natl. Acad. Sci. USA* 1987; 84:4846
22. Kane, W. H., Ichinose, A., Hagen, F. S. and Davie, E. W. *Biochemistry* 1987; 26:6508–6514
23. Cripe, L. D., Moore, K. D., and Kane, W. H. *Biochemistry* 1992; 31:3777–3785
24. Fass, D. N., Hewick, R. M., Knutson, G. J., Nesheim, M. E., and Mann, K. G. *Proc. Natl. Acad. Sci. USA* 1985; 82:1688–1691
25. Toole, J. J., Knopt, J. L., Wozney, J. M., Sultzman, L. A., Buecker, J. L., Pittman, D. D., Kaufman, R. J., Brown, E., Shoemaker, C., Orr, E. C., Amphlett, G. W., Foster, W. B., Coe, M. L., Knutson, G. J., Fass, D. N., and Hewick, R. M. *Nature* 1984; 312:342–347
26. Church, W. R., Jernigan, R. L., Toole, J., Hewick, R. M., Knopf, J., Knutson, G. J., Nesheim, M. E., Mann, K. G., and Fass, D. N. *Proc. Natl. Acad. Sci. USA* 1984; 81:6934–6937
27. Esmon, C. T. *Arterioscl. and Thromb.* 1992; 12:135–145
28. Walker, F. J. & Fay P. J. *FASEB. J.* 1992; 6:2561–2567
29. Walker, F. J. *J. Biol. Chem.* 1980; 255:5521–5524
30. Engesser, L., Broekmans, A. W., Briët, E., Brommer, E. J. P. & Bertina, R. M. *Ann. Int. Med.* 1987; 106:677–682
31. Hirsh, J., Piovella, F. & Pini, M. *Am. J. Med.* 1989; 87:345–385
32. Allaart, C. F. & Briët, E. In: *Haemostasis and Thrombosis* (Eds. Bloom, A. L., Forbes, C. D. & Thomas, D. P.

& Tuddenham E. G. D.) 1349–1360 (Churchill Livingstone London, 1994).
33. Wang, H., Riddell, D. C., Quinto, E. R. & MacGillivray, R. T. A. *Genomics* 1988; 2:324
34. Kalafatis, M. Rand, M. D., Jenny, R. J., Ehrlich, Y. M. & Mann, K. G., Blood 1993; 81: 704–719
35. Walker, F. J., Scandella, D. & Fay, P. J. *J. Biol. Chem.* 1990; 265:1484–1489
36. Walker, F. J. & Fay, P. J., *J. Biol. Chem.* 1990; 265:1834–1836
37. Suzuki, K., Dahlbäck, B & Stenflo, J. *J. Biol. Chem.* 1982; 257:6556–6564
38. Monkovic, D. D. & Tracey, P. B. *Biochemistry* 1990; 29:1118–1128 (1990).
39. Yang, X. J., Blajchman, M. A., Craven, S., Smith, L. M., Anvari, N. & Ofosu, F. A. *Biochem J.* 1990; 272:399–406
40. Triglia, T., Peterson, M. G., & Kemp, D. J. *Nucl. Acids Res.* 1988; 16:8186
41. NIH/CEPH collaborative mapping group. *Science* 1992: 258;67–86
42. Reitsma, P. H., Poort, S. R., Allaart, C. F., Briët, E. & Bertina, R. M. *Blood* 1991; 78: 890–894
43. Guinto E. R., Esmon, C. T., Mann K. G. & MacGillivray R. T. A. *J. Biol. Chem.,* 1992; 267:2971–2978
44. Pieters J. & Lindhout, T. *Blood* 1988; 72:2048–2052
45. Chromczynski, P. & Sacchi, N *Anal. Biochem.* 1987; 162:156–159
46. Verduyn, W., Doxiadis, I. I. N., Anholts J., Drabbels, J. J. M., Naipal, A., D'Amaro, J., Persyn, G. G., Giphart, M. J. & Schreuder, M. Th. *Hum. Immunol.* 1993; 37: 59–67
47. Faioni, E. M., Franchi, F., Asti, D., Sacchi, E., Bernardi, F., & Mannucci, P. M. *Thromb. Haemostas.* 1993; 70:1067–1071
48. Kalafatis, M., & Mann, K. *J. Biol. Chem.* 1993; 268:27246–27257
49. Fay, P. J., Smudzin, T. M. & Walker, F. J. *J. Biol. Chem.* 1991; 266:20139–20145
50. Odegaard, B., Mann, K. G.: Proteolysis of factor Va by factor Xa and activated protein C. J. Biol. Chem. 262: 11233–11238; 1987
51. Kalafatis, M., Haley, P. E., Mann, K. G.: Membrane-bound human factor Va is inactivated by activated protein C after cleavage of the heavy chain at Arg506 and Arg306. Blood 82, suppl. 1, p. 58a; 1993
52. Kalafatis, M., Rand, M. D., Mann, K. G.: Journ. of biological Chem. vol. 269, (1994), p31869–31880.

What is claimed is:

1. A method for determining whether a test person is homozygotic or heterozygotic for a mutation in Factor V and/or Factor Va or Factor VIII and/or Factor VIIIa comprising carrying out a method for determining whether a defect is present in response to APC, comprising adding APTT reagent and $CaCl_2$ in an amount of more than 25 mM to a sample to be tested and further carrying out determination of a value for a parameter known to be useful for diagnosis of the defect, and comparing the value obtained with a value obtained in the same manner for a sample from a normal individual or from an individual known to be homozygotic or heterozygotic, thereby establishing whether the test person is homozygotic or heterozygotic for a mutation in Factor V and/or Factor Va or Factor VIII and/or Factor VIIIa.

2. A method for determining whether a test person is homozygotic or heterozygotic for a mutation in Factor V and/or Factor Va or Factor VIII and/or Factor VIIIa comprising carrying out a method for determining whether a defect is present in anticoagulant response to APC, comprising adding APTT reagent and $CaCl_2$ in an amount of more than 25 mM to a sample to be tested and further carrying out determination of a value for a parameter known to be useful for diagnosis of the defect, and ascertaining the test person is abnormal when the result is a value below 0.84, to thereby establish whether the test person is homozygotic or heterozygotic for a mutation in Factor V and/or Factor Va or Factor VIII and/or Factor VIIIa.

3. A method of diagnosis of an increased risk of a thrombotic event comprising carrying out a method according to claims 1 or 2.

4. The method according to claim 1, wherein said mutation is in Factor V and/or Factor Va.

5. The method according to claim 1, wherein said mutation is in Factor V.

6. The method according to claim 1, wherein said mutation is in Factor Va.

7. The method according to claim 1, wherein said mutation is in Factor VIII and/or Factor VIIIa.

8. The method according to claim 1, wherein said mutation is in Factor VIII.

9. The method according to claim 1, wherein said mutation is in Factor VIIIa.

10. The method according to claim 2, wherein said mutation is in Factor V and/or Factor Va.

11. The method according to claim 2, wherein said mutation is in Factor V.

12. The method according to claim 2, wherein said mutation is in Factor Va.

13. The method according to claim 2, wherein said mutation is in Factor VIII and/or Factor VIIIa.

14. The method according to claim 2, wherein said mutation is in Factor VIII.

15. The method according to claim 2, wherein said mutation is in Factor VIIIa.

* * * * *

UNITED STATES PATENT AND TRADEMARK OFFICE
CERTIFICATE OF CORRECTION

PATENT NO. : 6,558,913 B1
DATED : May 6, 2003
INVENTOR(S) : Bertina et al.

It is certified that error appears in the above-identified patent and that said Letters Patent is hereby corrected as shown below:

<u>Title page,</u>
Item [73], Assignee, please delete "Akzo Nobel, N.V. (NL)" and substitute therefor:
-- Rijks Universiteit Leiden (NL) --

Signed and Sealed this

Thirty-first Day of August, 2004

JON W. DUDAS
*Director of the United States Patent and Trademark Office*